United States Patent

Takasugi et al.

[11] Patent Number: 5,217,971
[45] Date of Patent: Jun. 8, 1993

[54] THIAZOLE COMPOUNDS AND PHARMACEUTICAL COMPOSITION COMPRISING THE SAME

[75] Inventors: Hisashi Takasugi; Shigetaka Nishino, both of Osaka; Akito Tanaka, Takarazuka, all of Japan

[73] Assignee: Fujisawa Pharmaceutical Co., Ltd., Osaka, Japan

[21] Appl. No.: 637,943

[22] Filed: Jan. 8, 1991

Related U.S. Application Data

[63] Continuation of Ser. No. 451,935, Dec. 18, 1989, abandoned.

Foreign Application Priority Data

Jan. 5, 1989 [GB] United Kingdom ............... 8900191
Mar. 22, 1989 [GB] United Kingdom ............... 8906575

[51] Int. Cl.$^5$ ............... A61K 31/495; C07D 417/06
[52] U.S. Cl. ............................ 514/252; 544/369
[58] Field of Search ..................... 544/369; 514/252

[56] References Cited

U.S. PATENT DOCUMENTS 3,557,135  1/1971  Marchetti .............. 544/369 X
4,168,315  9/1979  Rymbrandt et al. ........ 544/369 X Primary Examiner—Mary C. Lee
Assistant Examiner—Jacqueline Haley
Attorney, Agent, or Firm—Oblon, Spivak, McClelland, Maier & Neustadt

[57] ABSTRACT

Thiazole compounds of the formula

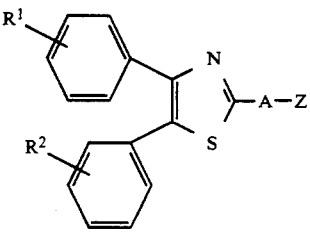

wherein the substituents are defined herein are disclosed as having antithrombotic, vasodilating, antiallergic, antiinflammatory and 5-lipoxygenase inhibitory activity.

10 Claims, No Drawings

THIAZOLE COMPOUNDS AND PHARMACEUTICAL COMPOSITION COMPRISING THE SAME

This application is a continuation of application Ser. No. 07/451,935, filed on Dec. 18, 1989, now abandoned.

This invention relates to new thiazole compounds. More particularly, this invention relates to new thiazole compounds and pharmaceutically acceptable salts thereof which have pharmacological activities, processes for preparation thereof, a pharmaceutical composition comprising the same and a use of the same.

Accordingly, on object of this invention is to provide the new and useful thiazole compounds and pharmaceutically acceptable salts thereof which possess antithrombotic, vasodilating, antiallergic, antiinflammatory and 5-lipoxygenase inhibitory activities.

Another object of this invention is to provide processes for preparation of the thiazole compounds and salt thereof.

A further object of this invention is to provide a pharmaceutical composition comprising said thiazole compounds or a pharmaceutically acceptable salt thereof.

Still further object of this invention is to provide a use of said thiazole compound or a pharmaceutically acceptable salts thereof as a medicament for prophylactic and therapeutic treatment of thrombosis, hypertension, cardiovascular or cerebrovascular diseases, allergy and inflammation, particularly thrombosis, in human being and animals.

The object thiazole compounds of the present invention are novel and represented by the following general formula:

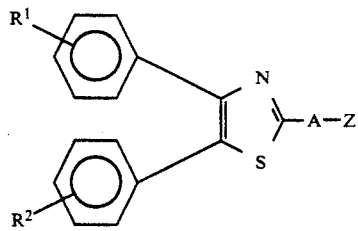

wherein
$R^1$ and $R^2$ are each halogen, lower alkyloxy, lower alkylthio or lower alkylsulfinyl,
A is lower alkylene, carbonyl or single bond, and
Z is heterocyclic group which may have suitable substituent(s), a group of the formula:

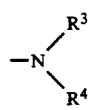

in which
$R^3$ and $R^4$ are each hydrogen, lower alkyl which may have heterocyclic group or piperidyl which may have suitable substituent(s),
or a group of the formula:

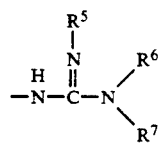

in which (1) $R^5$, $R^6$ and $R^7$ are each hydrogen, lower alkyl or cyclo(lower)alkyl;

(2) $R^5$ is hydrogen, lower alkyl, or cyclo(lower)alkyl, and $R^6$ and $R^7$ are linked together with the attached nitrogen atom to form heterocyclic group which may have suitable substituents(s); or (3) $R^5$ and $R^6$ are linked together to form lower alkylene, and $R^7$ is hydrogen;

provided that when Z is a group of the formula:

wherein $R^3$ and $R^4$ are each defined above, then A is lower alkylene or carbonyl.

The object compound (I) of the present invention can be prepared by the following processes:

Process (a)

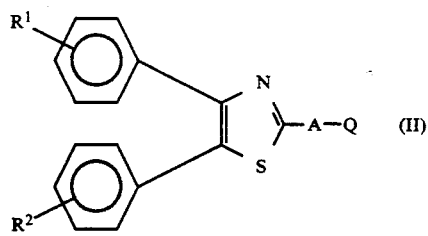

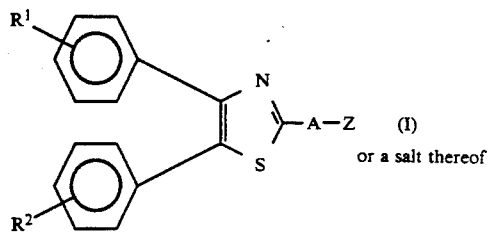

Process (b)
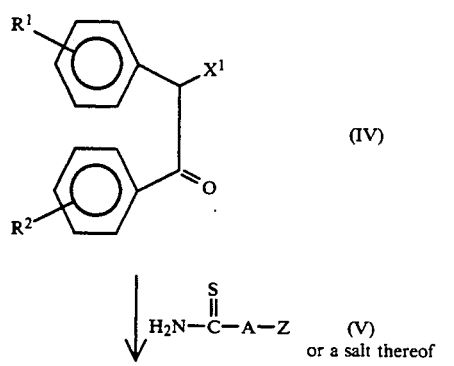
↓ $H_2N-\overset{\overset{S}{\|}}{C}-A-Z$  (V)
or a salt thereof
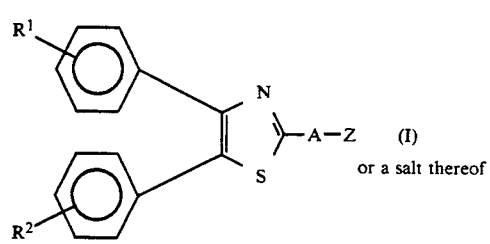
Process (c)
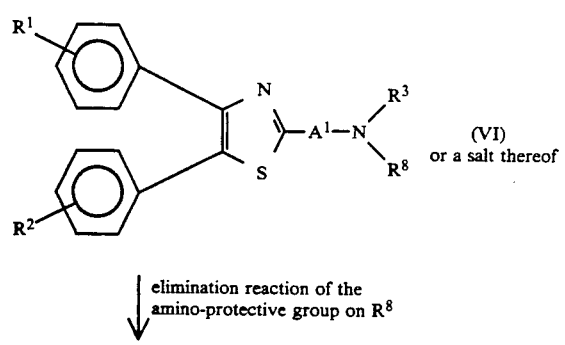
↓ elimination reaction of the
amino-protective group on $R^8$
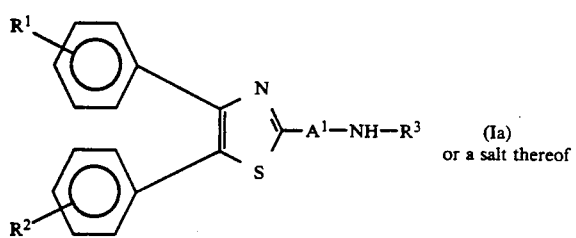
Process (d)
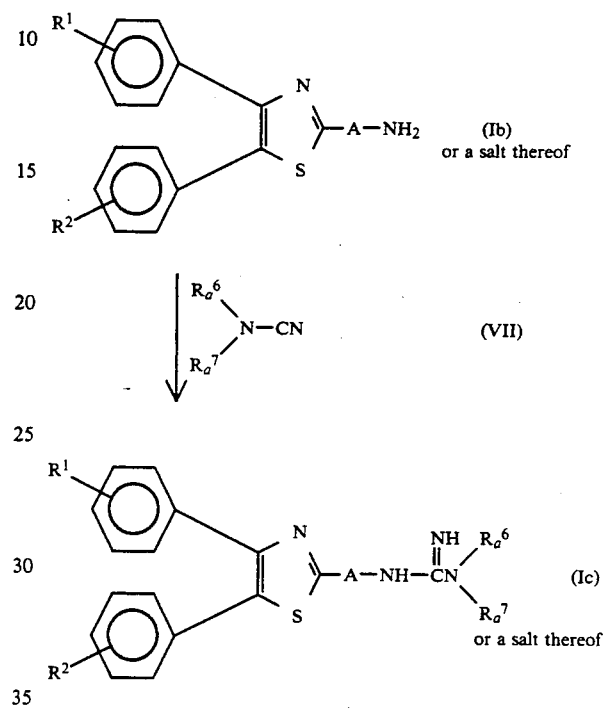
Process (e)
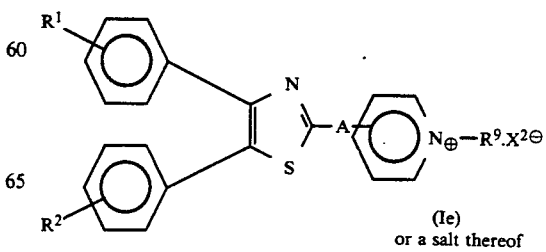

Process (f)
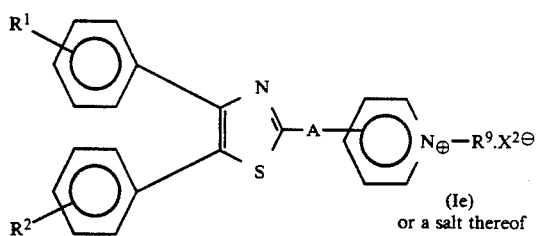
(Ie) or a salt thereof
↓ reduction
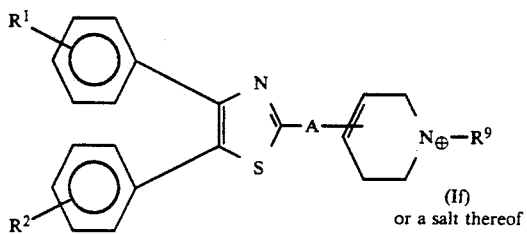
(If) or a salt thereof
Process (g)
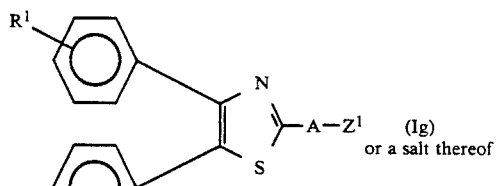
(Ig) or a salt thereof
↓ oxidation
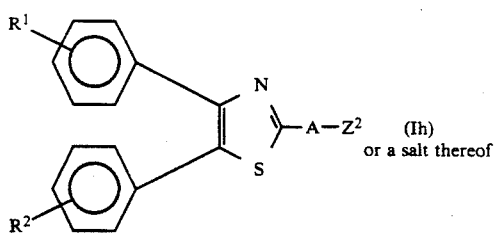
(Ih) or a salt thereof
Process (h)
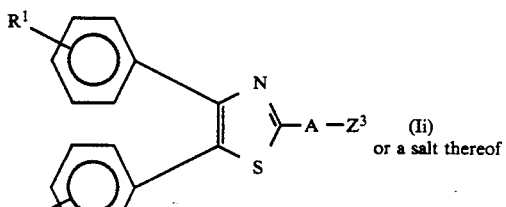
(Ii) or a salt thereof
↓ acylating reaction
-continued
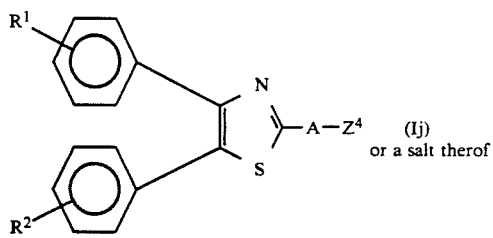
(Ij) or a salt thereof
Process (i)
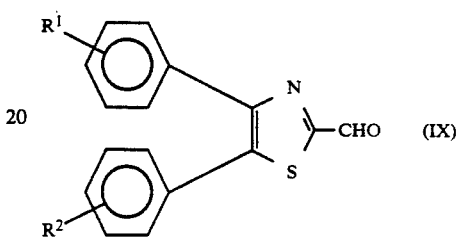
(IX)
↓ 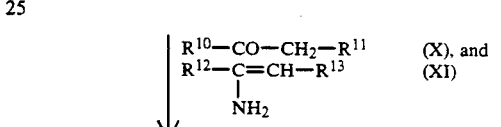
(X), and (XI)
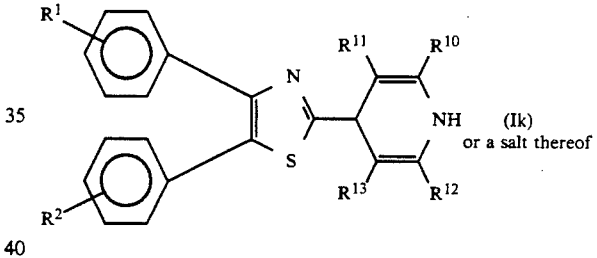
(Ik) or a salt thereof
Process (j)
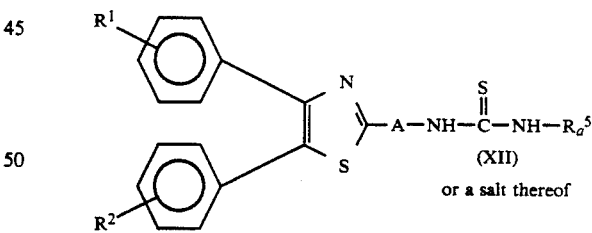
(XII) or a salt thereof
↓ 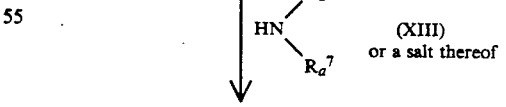
(XIII) or a salt thereof
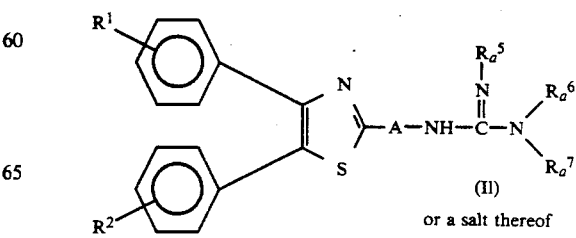
(Il) or a salt thereof Process (k)

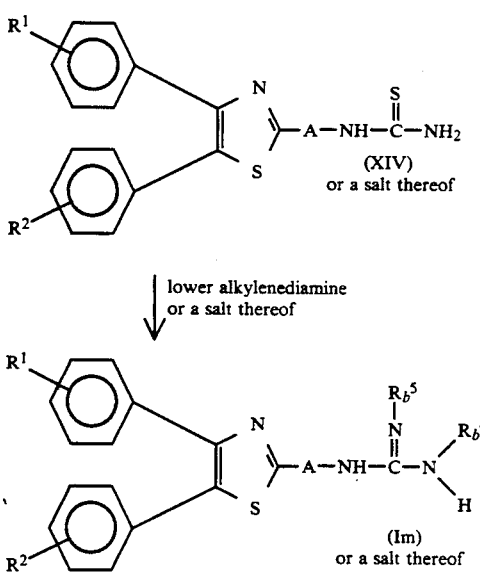

wherein
R¹, R², R³, A and Z are each as defined above,
$R_a^5$, $R_a^6$ and $R_a^7$ are each hydrogen, lower alkyl or cyclo(lower)alkyl, or
$R_a^6$ and $R_a^7$ are linked together with the attached nitrogen atom to form heterocyclic group which may have suitable substituent(s),
$R_b^5$ and $R_b^6$ are linked together to form lower alkylene,
R⁸ is amino-protective group,
R⁹, R¹⁰ and R¹² are each lower alkyl,
R¹¹ and R¹³ are each carboxy or a protected carboxy group,
A¹ is lower alkylene or carbonyl,
Q is suitable leaving group,
X¹ and X² are each an acid residue,
Z¹ is heterocyclic group having at least one nitrogen or one sulfur atom in its cyclic ring,
Z² is heterocyclic group having at least one oxidized nitrogen or one oxidized sulfur atom in its cyclic ring,
Z³ is heterocyclic group having an imino moiety in its cyclic ring, and
Z⁴ is heterocyclic group having acylimino moiety in its cyclic ring.

In the present invention, with regard to the object compound (I), (Ia), (Ib), (Ic), (Id), (Ie), (If), (Ig), (Ih), (Ii), (Ij), (Il) and (Im) and the starting compound (II), (VI), (XII) and (XIV) and when A or A¹ is lower alkylene, it is to be understood that there may be tautomeric equilibrium between the partial structures of such compound as follows:

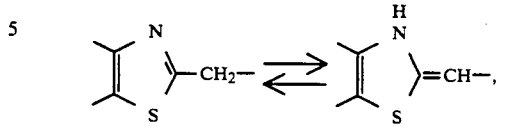

and such tautomer is also included within the scope of the present invention.

However, in the present invention, the partial structure of the compounds (I), (Ia), (Ib), (Ic), (Id), (Ie), (If), (Ig), (Ih), (Ii), (Ij), (Il), (Im), (II), (VI) and (XIV) in case A or A¹ is lower alkylene, are represented by the following one expression for convenient sake,

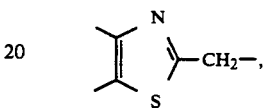

and the compounds (I), (Ia), (Ib), (Ic), (Id), (Ie), (If), (Ig), (Ih), (Ii), (Ij), (Il), (Im), (II), (VI) and (XIV) are named on the basis of such formula, when A or A¹ is lower alkylene.

And, with regard to the object compound (I), (Ic), (II) and (Im) and the starting compounds (II), (XII) and (XIV), it is to be understood that there may be tautomeric equilibrium between the partial structures of such compounds as follows:

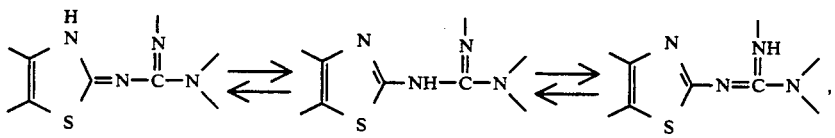

and

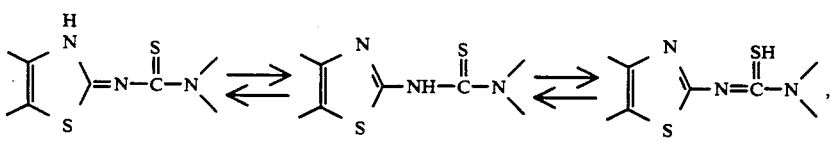

and these tautomers are also included within the scope of the present invention.

However, in the present invention, the partial structure of the compounds (I), (Ic), (II), (Im), (II), (XII) and (XIV) are represented by one expression for convenient sake, that is by the following formulae:

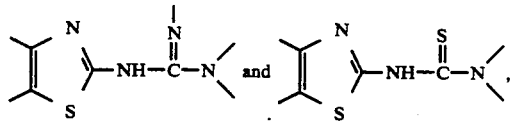

and the compounds (I), (Ic), (II), (Im), (II), (XII) and (XIV) are named on the basis of such formulae.

Suitable pharmaceutically acceptable salts of the object compounds (I), (Ia), (Ib), (Ic), (Id), (If), (Ih), (Ii), (Ij), (Ik), (Il) or (Im) are conventional non-toxic salts and may include e.g. a salt with a base or an acid addition salt such as a salt with an inorganic base, for example, an alkali metal salt (e.g. sodium salt, potassium salt, etc.), an alkaline earth metal salt (e.g. calcium salt, magnesium salt, etc.) an ammonium salt; a salt with an organic base, for example, an organic amine salt, (e.g. triethylamine salt, pyridine salt, picoline salt, ethanolamine salt, triethanolamine salt, dicyclohexylamine salt, N,N'-dibenzylethylenediame salt, etc.); an inorganic acid addition salt (e.g. hydrochloride, hydrobromide, sulfate, phosphate, etc.); an organic carboxylic or sulfonic acid addition salt (e.g. formate, acetate, trifluoroacetate, maleate, tartrate, methanesulfonate, benzenesulfonate, toluenesulfonate, etc.); a salt with a basic or acidic amino acid (e.g. arginine, aspartic acid, glutamic acid, etc.).

In the above and subsequent descriptions of the present specification, suitable examples and illustration of the various definitions which the present invention intends to include within the scope thereof are explained in detail as follows.

The term "lower" is used to intend a group having 1 to 6, preferably 1 to 4, carbon atoms(s), unless otherwise provided.

Suitable "lower alkyl" and lower alkyl moiety in the term "lower alkyloxy", "lower alkylthio", "lower alkylsulfinyl" and "lower alkyl which may have heterocyclic group" may include straight or branched one having 1 to 6 carbon atom(s), such as methyl, ethyl, propyl, isopropyl, butyl, isobutyl, sec-butyl, tert-butyl, pentyl, tert-pentyl, hexyl, and the like, preferably one having 1 to 4 carbon atom(s).

Suitable "lower alkylene" may be straight or branched one having 1 to 6 carbon atom(s), such as methylene, ethylene, trimethylene, propylene, tetramethylene, pentamethylene, hexamethylene, and the like, preferably one having 1 to 4 carbon atom(s), and the most preferably methylene.

Suitable "cyclo(lower)alkyl" may include 3 to 8 membered cycloalkyl such as cyclopropyl, cyclobutyl, cyclopentyl, cyclohexyl, cycloheptyl, cyclooctyl, and the like, preferably one having 5 to 7 carbon atoms.

Suitable "halogen" may be fluorine, chlorine, bromine or iodine.

Suitable "heterocyclic group" in "heterocyclic group which may have suitable substituent(s)" and "lower alkyl which may have heterocyclic group" may be aliphatic or aromatic, heteromonocyclic or heteropolycylic group containing at least one hetero atom such as nitrogen, oxygen and sulfur atoms, and more suitable "heterocyclic group" thus defined may include 5 to 7 membered aliphatic heteromonocyclic group having one to three hetero atom(s) selected from nitrogen, oxygen and sulfur or 5 to 6 membered aromatic heteromonocyclic group having one to three hetero atom(s) selected from nitrogen, oxygen and sulfur, such as piperidyl, piperazinyl, morpholinyl, thiomorpholinyl, pyridyl, dihydropyridyl, tetrahydropyridyl, perhydrodiazepinyl, tetrahydropyridazinyl, and the like.

Suitable substituent on such heterocyclic group and "piperidyl" may include amino; hydroxy; amino; cyano; lower alkyl as exemplified above; lower alkoxy as exemplified above; hydroxy(lower)alkyl in which the lower alkyl moiety may be the same as those exemplified above; acyl(lower)alkyl, the acyl group of which may be the same as those exemplified below, preferably carbamoyl(lower)alkyl (e.g. carbamoylmethyl, carbamoylethyl, etc.), lower alkylcarbamoyl(lower)alkyl (e.g. methylcarbamoylmethyl, ethylcarbamoylmethyl, propylcarbamoylmethyl, isopropylcarbamoylmethyl, methylcarbamoylethyl, etc.); oxo; acyl as exemplified below, preferably lower alkylcarbamoyl (e.g. methylcarbamoyl, ethylcarbamoyl, propylcarbamoyl, isopropylcarbamoyl, butylcarbamoyl, hexylcarbamoyl, etc.), lower alkanoyl (e.g. formyl, acetyl, propionyl, butyryl, pentanoyl, hexanoyl, pivaloyl, etc.), etc.; protected amino such as acylamino, in which the acyl moiety may be the same as those exemplified below, preferably lower alkanoylamino (e.g. formylamino, acetylamino, propionylamino, butyrylamino, valerylamino, hexanoylamino, pivaloylamino, etc.); carboxy; protected carboxy such as esterified carboxy, for example lower alkoxycarbonyl (e.g. methoxycarbonyl, ethoxycarbonyl, propoxycarbonyl, isopropoxycarbonyl, butoxycarbonyl, hexyloxycarbonyl, neopentyloxycarbonyl, etc.); ar(lower)alkyl such as mono or di or triphenyl(lower)alkyl (e.g. benzyl, benzhydryl, trityl, phenethyl, etc.); and the like.

Suitable examples of the said acyl may be aliphatic, aromatic acyl derived from carboxylic, carbonic, sulfonic and carbamic acid such as lower alkanoyl (e.g., formyl, acetyl, propionyl, butyryl, isobutyryl, valeryl, isovaleryl, oxalyl, succinyl, pivaloyl, etc.), preferably one having 1 to 4 carbon atom(s); more preferably one having 1 to 2 carbon atom(s); lower alkoxycarbonyl having 2 to 7 carbon atoms (e.g., methoxycarbonyl, ethoxycarbonyl, propoxycarbonyl, 1-cyclopropylethoxycarbonyl, isopropoxycarbonyl, butoxycarbonyl, t-butoxycarbonyl, pentyloxycarbonyl, t-pentyloxycarbonyl, hexyloxycarbonyl, etc.), preferably one having 3 to 6 carbon atoms; lower alkanesulfonyl (e.g., mesyl, ethanesulfonyl, propanesulfonyl, isopropanesulfonyl, butanesulfonyl, etc.); arenesulfonyl (e.g., benzenesulfonyl, tosyl, etc.); aroyl (e.g., benzoyl, toluoyl, naphthoyl, phthaloyl, indancarbonyl, etc.); ar(lower)alkanoyl (e.g. phenylacetyl, phenylpropionyl, etc.); cyclo(lower)alkyl(lower)alkanoyl (e.g. cyclohexylacetyl, cyclopentylacetyl, etc.); ar(lower)alkoxycarbonyl (e.g. benzyloxycarbonyl, phenethyloxycarbonyl, etc.); and the like:

Suitable "leaving group" is a group which is capable of replacing with a group of the formula:

-Z (wherein Z is as defined above), preferably halogen (e.g., fluorine, chlorine, bromine, iodine, etc.), acyloxy (e.g., acetoxy, methanesulfonyloxy, etc.) or lower alkyloxy which can be the same as described in the above.

Suitable "acid residue" may be halogen (e.g. chlorine, bromine, iodine or fluorine); acyloxy such as lower alkanoyloxy (e.g. acetoxy, etc.), lower alkanesulfonyloxy (e.g. methanesulfonyloxy, etc.), and the like, and preferably halogen.

Suitable "amino-protective group" may be acyl, which may be the same as described in the above.

Suitable "protected carboxy group" may be esterified carboxy group, which may be the same as described in the above.

Suitable acyl moiety of the "acylamino" in $Z^4$ may be the same as described in the above. "Heterocyclic group which may have suitable substituent(s)" formed by linking together with the attached nitrogen atom for $R^6$ and $R^7$ or $R_a^6$ and $R_a^7$ may be the same as those explained above, in which the heterocyclic group has at least one nitrogen atom and the binding radical comes from the said nitrogen atom such as piperazine-1-yl, lower alkylpiperazine-1-yl, morpholino, thiomorpholino, and the like.

Suitable "heterocyclic group having at least one nitrogen or one sulfur atom in its cyclic ring" may be the same as the heterocyclic group as explained above, in which the heterocyclic group has at least one nitrogen atom or one sulfur atom such as piperazinyl (e.g. piperazin-1-yl, etc.), 4-lower alkylpirepazinyl (e.g. 4-methylpiperazin-1-yl, etc.), thiomorpholino, and the like.

Suitable "heterocyclic group having at least one oxidized nitrogen or one oxidized sulfur atom in its cyclic ring" may be the same as the heterocyclic group as explained above, in which the heterocyclic group has at least one oxidized nitrogen atom or one oxidized sulfur atom such as 4-oxopiperazinyl (e.g. 4-oxopiperazine-1-yl, etc.), 4-lower alkyl-4-oxopiperazinyl (e.g. 4-methyl-4-oxopirepazin-1-yl, etc.), 1-mono or 1,1-dioxothiomorpholino, and the like.

Suitable "heterocyclic group having an imino moiety in its cyclic ring" may be the same as those explained above, in which the heterocyclic group has an imino moiety such as piperazinyl (e.g. piperazin-1-yl, etc.), and the like.

Suitable "heterocyclic group having an acylimino moiety in its cyclic ring" may be the same as those explained above, in which the heterocyclic group has an imino moiety and the said imino moiety is substituted by acyl such as 4-lower alkanoylpiperazinyl (e.g. 4-acetylpiperazin-1-yl, etc.), lower alkylcarbamoyl (e.g. isopropylcarbamoyl, etc.), and the like.

Particularly, suitable examples of "heterocyclic group which may have suitable substituent(s)" in Z may be piperazinyl; lower alkylpiperazinyl (e.g. 4-methylpiperazin-1-yl, etc.); hydroxy(lower)alkylpiperazinyl [e.g. 4-(2-hydroxyethyl)piperazin-1-yl, etc.]; acylpiperazinyl such as lower alkanoylpiperazinyl (e.g. 4-acetylpiperazin-1-yl, etc.), lower alkylcarbamoylpiperazinyl (e.g. 4-isopropylcarbamoylpiperazin-1-yl, etc.) etc.; acyl(lower)alkylpiperazinyl such as lower alkylcarbamoyl(lower)alkylpiperazinyl (e.g. 4-isopropylcarbamoylmethylpiperazin-1-yl, etc.); lower alkyl and oxo-disubstituted piperazinyl (e.g. 4-methyl-4-oxopiperazin-1-yl, etc.); morpholinyl (e.g. morpholino, etc.); thiomorpholinyl (e.g. thiomorpholino, etc.); dioxothiomorpholinyl (e.g. 1,1-dioxothiomorpholino, etc.); piperidyl (e.g. piperidino, etc.); hydroxy(lower)alkylpiperidyl [e.g. 2-(2-hydroxyethyl)piperidino, etc.); acylaminopiperidyl such as lower alkanoylaminopiperidyl (e.g. 4-acetylaminopiperidino, etc.), etc.; lower alkylperhydrodiazepinyl (e.g. 4-methyl-1,4--perhydrodiazein-1-yl, etc.); pyridyl (e.g. 4pyridyl, etc.); lower alkylpyridyl (e.g. 1-methyl-4-pyridyl, etc.); lower alkyltetrahydropyridyl (e.g. 1-methyl-1,2,5,6-tetrahydro-4-pyridyl, etc.); one or two protected carboxy and one or two lower alkyl-substituted dihydropyridine such as bis(lower alkyloxycarbonyl)-di(lower)alkyldihydropyridyl [e.g. 3,5-bis(ethoxycarbonyl)-2,6-dimethyl-1,4-dihydro-4-pyridyl, etc.)etc.; or oxo-tetrahydropyridazinyl (e.g. 6-oxo-1,4,5,6-tetrahydropyridazin-3yl, etc.).

And, suitable examples of "lower alkyl which may have heterocyclic group" in $R^3$ and/or $R^4$ may be morpholinyl(lower)alkyl e.g. 2-morpholineotethyl, etc.), pyridyl(lower)alkyl (e.g. 2-morpholinoethyl, etc.), pyridyl(lower)alkyl [e.g. 2-(2-pyridyl)ethyl, etc.], and the like.

And, suitable examples of "piperidyl which may have suitable substituent(s)" may be ar(lower)alkylpiperidyl such as mono or di or triphenyl(lower)alkylpiperidyl (e.g. 1-benzylpiperidin-4-yl, etc.), and the like.

The processes for preparing the object compound (I) are explained in detail in the following:

Process (a)

The object compound (I) or a salt thereof can be prepared by reacting the compound (II) with the compound (III) or a salt thereof.

Suitable salts of the compound (III) can be referred to the ones as exemplified for the compound (I).

The reaction is usually carried out in a conventional solvent such as alcohols (e.g. methanol, ethanol, ethylene glycol, etc.), chloroform, ether, tetrahydrofuran, benzene or any other organic solvent which does not adversely influence the reaction.

The reaction temperature is not critical and the reaction is usually carried out under cooling to heating.

The reaction may be also carried out in the presence of an inorganic or an organic base such as alkali metal hydroxide, an alkali metal hydrogencarbonate, alkali metal carbonate, alkali metal acetate, tri(lower)alkylamine, pyridine (e.g. pyridine, lutidine, picoline, dimethylaminopyridine, etc.), N-(lower)alkylmorpholine, N,N-di(lower)alkylbenzylamine, N,N-di(lower)alkylaniline or the like. When the base and/or the starting compound are in liquid, they can be used also as a solvent.

Process (b)

The object compound (I) or a salt thereof can be prepared by reacting the compound (IV) with the compound (V) or a salt thereof.

Suitable salts of the compound (V) can be referred to the ones as exemplified for the compound (I).

The reaction is usually carried out in a conventional solvent such as water, alcohols (e.g. methanol, ethanol, isopropyl alcohol, etc.), tetrahydrofuran, dioxane, chloroform, methylene chloride, dimethyl acetamide, N,N-dimethylformamide or any other organic solvent which does not adversely influence the reaction. Among these solvents, hydrophilic solvents may be used in a mixture with water.

The reaction temperature is not critical and the reaction is usually carried out under cooling to heating.

This reaction may also be carried out in the present of an inorganic or an organic base as defined above in Process (a).

Process (c)

The compound (Ia) or a salt thereof can be prepared by subjecting the compound (VI) or a salt thereof to elimination reaction of the amino-protective group on $R^8$.

Suitable method for this elimination reaction may include conventional one such as hydrolysis.

Hydrolysis is preferably carried out in the presence of an acid or a base.

Suitable acid may be an inorganic acid (e.g. hydrochloric acid, hydrobromic acid, sulfuric acid, etc.), an organic acid (e.g. formic acid, acetic acid, trifluoroacetic acid, propionic acid, methanesulfonic acid, benzenesulfonic acid, p-toluenesulfonic acid, etc.), an acidic ion-exchange resin and the like. In case that the organic acid such as trifluoroacetic acid and p-toluenesulfonic acid is used in this reaction, the reaction is preferably carried out in the presence of cation trapping agents (e.g. anisole, etc.).

The acid suitable for his hydrolysis can be selected according to the kinds of the amino-protective group to be eliminated, for example, this hydrolysis can preferably be applied to the amino-protective group for $R^8$ such as lower alkoxycarbonyl or lower alkanoyl.

Suitable base may include an inorganic base and an organic base such as an alkali metal (e.g. sodium, potassium, etc.), an alkaline earth metal (e.g. magnesium, calcium, etc.), the hydroxide or carbonate or hydrogencarbonate thereof, trialkylamine (e.g. trimethylamine, triethylamine, etc.), picoline, 1,5-diazabicyclo[4.3.0]none-5ene, 1,4-diazabicyclo[2.2.2]octane, 1,8-diazabicyclo[5.4.0]undecene-7, or the like.

The hydrolysis is usually carried out in a conventional solvent which does not adversely influence the reaction such as water, methanol, ethanol, propanol, tert-butyl alcohol, tetrahydrofuran, N,N-dimethylformamide, dioxane or a mixture thereof, and further the above-mentioned acids can also be used as a solvent when they are in liquid.

The reaction temperature of this hydrolysis is not critical, and the reaction is usually carried out under cooling to heating.

Process (d)

The compound (Ic) or a salt thereof can be prepared by reacting the compound (Ib) or a salt thereof with the compound (VII).

The reaction is usually carried out in a conventional solvent such as water, alcohols (e.g., methanol, ethanol, isopropyl alcohol, etc.), tetrahydrofuran, dioxane, chloroform, methylene chloride, dimethyl acetamide, N,N-dimethylformamide or any other organic solvent which does not adversely influence the reaction. Among these solvents, hydrophilic solvents may be used in a mixture with water.

The reaction temperature is not critical and the reaction is usually carried out under cooling to heating.

Process (e)

The compound (Ie) or a salt thereof can be prepared by reacting the compound (Id) or a salt thereof, with the compound (VIII).

The reaction is usually carried out in a conventional solvent such as water, alcohol (e.g., methanol, ethanol, isopropyl alcohol, etc.), tetrahydrofuran dioxane, chloroform, methylene chloride, dimethyl acetamide, N,N-dimethylformamide or any other organic solvent which does not adversely influence the reaction. Among these solvents, hydrophilic solvents may be used in a mixture with water.

The reaction temperature is not critical and the reaction is usually carried out under cooling to heating.

Process (f)

The compound (If) or a salt thereof can be prepared by subjecting the compound (Ie) or a salt thereof to reduction.

Reduction is carried out in a conventional manner, which is capable of reducing a pyridine ring to a 1,2,5,6-tetrahydropyridine ring, including chemical reduction and catalytic reduction.

Suitable reducing agents to be used in chemical reduction are hydrides (e.g. hydrogen iodide, hydrogen sulfide, lithium aluminum hydride, sodium borohydride, etc.) or a combination of a metal (e.g. tin, zinc, iron, etc.) or metallic compound (e.g. chromium chloride, chromium acetate, etc.) and an organic or inorganic acid (e.g. formic acid, acetic acid, propionic acid, trifluoroacetic acid, p-toluenesulfonic acid, hydrochloric acid, hydrobromic acid, etc.).

Suitable catalysts to be used in catalytic reduction are conventional ones such as platinum catalysts (e.g. platinum plate, spongy platinum, platinum black, colloidal platinum, platinum oxide, platinum wire, etc.), palladium catalysts (e.g. spongy palladium, palladium black, palladium oxide, palladium on carbon, colloidal palladium, palladium on barium sulfate, palladium on barium carbonate, etc.), nickel catalysts (e.g. reduced nickel, nickel oxide, Raney nikel, etc.), cobalt catalysts (e.g. reduced cobalt, Raney cobalt, etc.), iron catalysts (e.g. reduced iron, Raney iron, etc.), copper catalysts (e.g. reduced cooper, Raney copper, Ullman copper, etc.) and the like.

The reduction is usually carried out in a solvent such as water, alcohol (e.g. methanol, ethanol, etc.), N,N-dimethylformamide, tetrahydrofuran, a mixture thereof or any other solvent which does not adversely affect the reaction.

Additionally, in case that the above-mentioned acids to be used in chemical reduction are in liquid, they can also be used as a solvent.

the reaction temperature of this reduction is not critical and the reaction is usually carried out under cooling to warming.

Process (g)

The object compound (Ih) or a salt thereof can be prepared by subjecting the compound (Ig) or a salt thereof to oxidation reaction.

Oxidation is carried out in a conventional manner, which is capable of oxidizing a nitrogen and/or sulfur atom(s) to an oxidized nitrogen and/or oxidized sulfur atom(s), and suitable oxidizing reagent may be oxygen acid such as periodate (e.g. sodium periodate, etc.), peroxy acid such as peroxybenzoic acids (e.g. peroxybenzoic acid, m-chloroperoxybenzoic acid, etc.), and the like.

The reaction is usually carried out in a conventional solvent such as water, alcohol (e.g., methanol, ethanol, isopropyl alcohol, etc.), tetrahydrofuran, dioxane, dichloromethane, chloroform, dimethyl acetamide, N,N-dimethylformamide or any other organic solvent which does not adversely influence the reaction. Among these solvents, hydrophilic solvents may be used in a mixture with water.

The reaction temperature is not critical and the reaction is usually carried out under cooling to heating.

In this reaction, lower alkylthio group for $R^1$ and $R^2$ are simultaneously oxidized to lower alkylsulfinyl or lower alkylsulfonyl, and such case is also included within the scope of the present reaction.

Process (h)

The object compound (Ij) or a salt thereof can be prepared by subjecting the compound (Ii) or a salt thereof to an acylating reaction.

The acylating reaction is carried out in a conventional manner under the existence of a suitable acylating agent which is capable of converting an imino moiety to an acylimino moiety.

The acyl group introduced by the acylating agent can be referred to one explained before.

Suitable acylating agent may be carboxylic, carbonic, sulfonic and carbamic acid and their reactive derivative such as acid halide (e.g. acid chloride, etc.), acid anhydride; activated ester; substituted isocyanate, for example N-(lower)alkylisocyanate (e.g. N-isopropyl isocyanate, etc.), and the like.

The reaction is usually carried out in a conventional solvent such as alcohol (e.g., methanol, ethanol, isopropyl alcohol, etc.), tetrahydrofuran, dioxane, dichloromethane, chloroform, dimethyl acetamide, N,N-dimethylformamide or any other organic solvent which does not adversely influence the reaction.

The reaction temperature is not critical and the reaction is usually carried out under cooling to warming.

Process (i)

The object compound (Ik) or a salt thereof can be prepared by reacting the compound (IX) with the compounds (X) and (XI).

The reduction is usually carried out in a conventional solvent such as water, alcohols (e.g. methanol, ethanol, isopropyl alcohol, etc.), tetrahydrofuran, dioxane, chloroform, methylene chloride, dimethyl acetamide, N,N-dimethylformamide or any other organic solvent which does not adversely influence the reaction. Among these solvents, hydrophilic solvents may be used in a mixture with water.

The reaction temperature is not critical and the reaction is usually carried out under cooling to heating.

Process (j)

The object compound (Il) or a salt thereof can be prepared by reacting the compound (XII) with the compound (XIII) or a salt thereof.

Suitable salts of the compound (XIII) can be referred to the ones as exemplified for the compound (I).

The reaction may be carried out in the presence of activating agents such as lower alkyl halide (e.g., methyl iodide, etc.), ar(lower)alkyl halide (e.g. benzyl iodide, etc.), or the like, which is capable of activating a substitution reaction of thiocarbonyl group ($>C=S$).

The reaction is usually carried out in a conventional solvent such as alcohol (e.g., methanol, ethanol, etc.), chloroform, ether, tetrahydrofuran, benzene or any other organic solvent which does not adversely influence the reaction.

The reaction temperature is not critical and the reaction is usually carried out under cooling to heating.

The reaction may be also carried out in the presence of an inorganic or an organic base such as an alkali metal hydroxide, an alkali metal hydrogencarbonate, alkali metal carbonate, alkali metal acetate, tri(lower)alkylamine, pyridine, N-(lower)alkylmorpholine, N,N-di(lower)alkylbenzylamine, N,N-di(lower)alkylaniline, or the like. When the base is in liquid, it can be used also as a solvent.

Process (k)

The compound (Im) or a salt thereof can be prepared by reacting the compound (XIV) with lower alkylenediamine or a salt thereof.

Suitable salts of lower alkylenediamine can be referred to the ones as exemplified for the compound (I).

This reaction can be carried out by substantially the same method as that illustrated for Process (j), and therefore reaction conditions (i.e. reaction temperature and solvent, etc.) are to be referred to said explanation.

The object compounds (I), (Ia), (Ib), (Ic), (Ie), (If), (Ih), (Ij), (Ik), (Il) and (Im) obtained by the above processes or salts thereof can be isolated and purified by using conventional manners in this field, such as column chromatography, recrystallization, or the like.

The compounds (I) may be converted into the aforesaid salts according to a conventional manner.

Some of the starting compounds in Process (a) to (k) are novel and can be prepared by the following processes:

Process ①

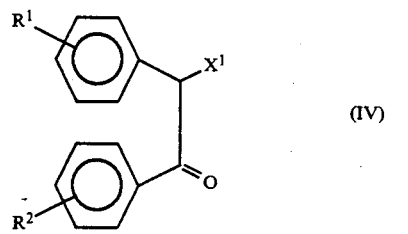

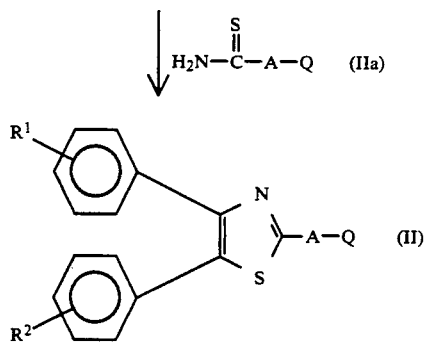

Process ②

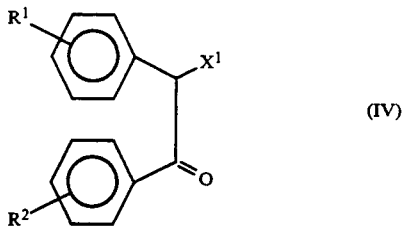

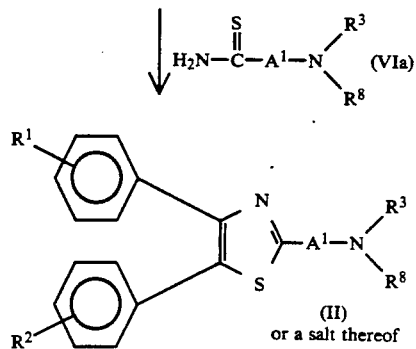

Process ③

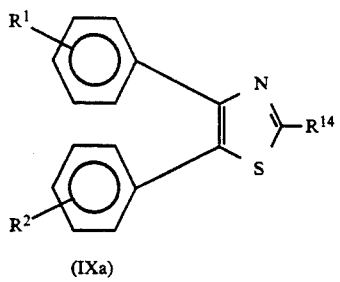

(IXa)

↓ reduction

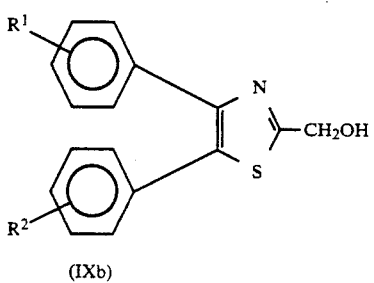

(IXb)

↓ oxidation

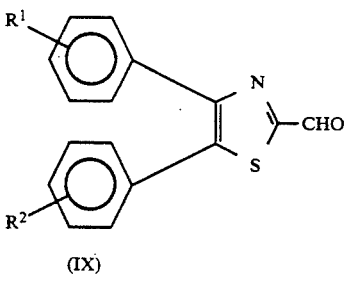

(IX)

Process ④

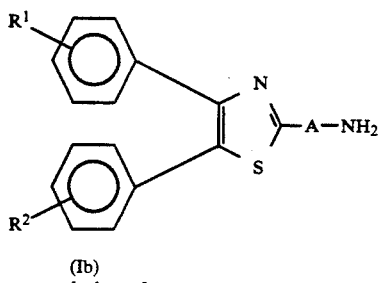

(Ib)
or a salt thereof

↓ S=C=N—$R_a^5$  (XIIa)

-continued

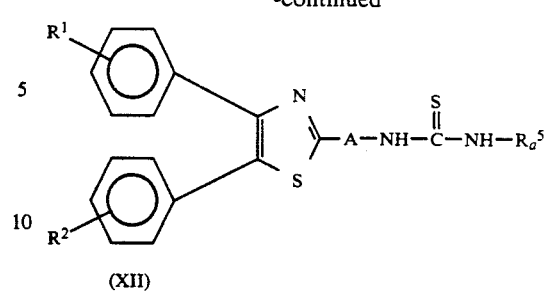

(XII)

Process ⑤

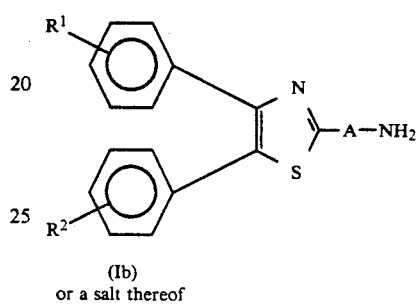

(Ib)
or a salt thereof

↓ S=C=N—$R^{15}$  (XIVa)

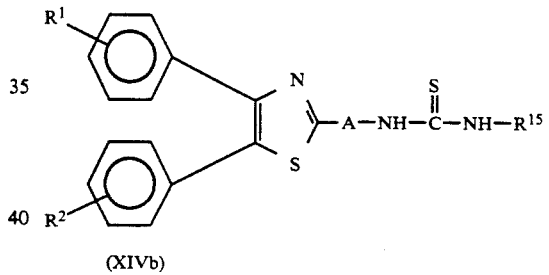

(XIVb)

↓ elimination reaction

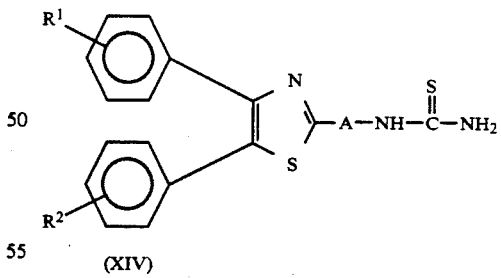

(XIV)

wherein
$R^1$, $R^2$, $R^3$, $R^8$, $R_a^5$, A, $A^1$, Q and $X^1$ are each as defined above.

$R^{14}$ is esterified carboxy such as those exemplified before and $R^{15}$ is acyl such as those exemplified before, preferably lower alkanoyl (e.g. acetyl, etc.) or aroyl (e.g. benzoyl, etc.).

Processes ① to ⑤ for the preparation of the starting compounds are explained in detail in the following.

Process ①

The compound (II) can be prepared by reacting the compound (IV) with the compound (IIa).

This reaction can be carried out in a similar manner to that of the aforementioned Process (b), and therefore the reaction conditions (e.g. base, solvent, temperature, etc.) can be referred to those of Process (b).

Process ②

The compound (VI) or a salt thereof can be prepared by reacting the compound (IV) with the compound (VIa). This reaction can be carried out in a similar manner to that of the aforementioned Process (b), and therefore the reaction conditions (e.g. solvent, temperature, base, etc.) can be referred to those of Process (b).

Process ③

The compound (IX) can be prepared by subjecting the compound (IXa) to a reduction, and further to an oxidation.

The said reduction can be carried out in a conventional manner by using a conventional reducing reagent which is capable of reducing an esterified carboxy group to a hydroxy methyl group such as lithium aluminum hydride, and the like.

And the said oxidation can also be carried out in a conventional manner by using a conventional oxidizing agent which is capable of oxidizing a hydroxymethyl group to a formyl group such as manganese dioxide, and the like.

Process ④

The compound (XII) can be prepared by reacting the compound (Ib) or a salt thereof with the compound (XIIa).

This reaction can be carried out in a similar manner to that of the aforementioned Process (h), and therefore the reaction condition (e.g. solvent, temperature, base, etc.) can be referred to those of Process (h).

Process ⑤

The compound (XIV) can be prepared by reacting the compound (Ib) or a salt thereof with the compound (XIVa), and further by subjecting the resulting compound (XIVb) to an elimination reaction of the acyl group in $R^{15}$, in a similar manner to that of the aforementioned Process (c).

The first and second steps of this process can be carried out in similar manners to Processes (h) and (c), respectively, and therefore the reaction conditions (e.g. solvent, temperature, etc.) can be referred to those of Processes (h) and (c).

The other starting compounds can be prepared in a similar manner to Processes ① to ⑤ or a conventional manner.

The new thiazole compounds (I) and a pharmaceutically acceptable salt thereof of the present invention possess strong antithrombotic activity inhibiting the activities against cyclooxygenase, thrombin, and the like, and/or inhibiting aggregation of platelet; vasodilating activity; anti-allergic activity; anti-inflammatory activity; and 5-lipoxygenase inhibitory activity; particularly antithrombotic activity, and therefore are useful as antithrombotic agent, vasodilating agent, anti-allergic agent, anti-inflammatory agent and 4-lipoxygenase inhibiting agent, particularly antithrombotic agent.

Accordingly, the new thiazole compounds (I) and a pharmaceutically acceptable salt thereof can be used for prophylactic and therapeutic treatment of cerebral thrombosis, atrophic thrombosis; coronary thrombosis; creeping thrombosis; dialation thrombosis; jumping thrombosis; mural thrombosis; placental thrombosis; platelet thrombosis; posttraumatic arterial thrombosis; thrombostasis; compression thrombosis; peripheral vascular disorders such as chronic arterial occulasion; transient ischemic attack; myocardial infarction; cerebral infarction; reocculusion after percutaneous transluminal coronary angioplasty or percutaneous transluminal coronary recanalization; arteriosclerosis; cerebiral vasospam; disseminated intravascular coagulopathy; hypertension such as pulmonary hypertension; asthma; psoriasis; hepatitis; pancreatitis; arthritis; nephritis; inflammatory bowel diseases; septic shock; rhinitis; conjunctivitis; epidermitis; rheumatism; peptic ulcer; gout; dysmnesia; senile dementia; Crohn's disease; adult respiratory disease syndrome; endotoxin shock; and the like.

And these compounds are also useful for inhibition of thrombosis during extracorporeal circulation such as dialysis.

Further, these compounds are also expected to have antipyretic activity, analgesic activity, antiviral activity, antifungal activity, and the like.

The thiazole compounds (I) and a pharmaceutically acceptable salt thereof scarcely have side effect exerting a bad influence upon patients.

In order to show the utilities of the thiazole compounds (I) and a pharmaceutically acceptable salt thereof of the present invention, pharmacological test data of the representative compound of the thiazole compounds (I) are illustrated in the following.

The expressions of "Example 1", "Example 3", "Example 5", Example 12", "Example 14" and "Example 21" in the following tests mean the compounds prepared in Examples 1, 3, 5, 12, 14 and 21, respectively.

Platelet aggregation ex vivo (1)

1. Test method

Male Hartley guinea-pigs weighing about 300 g were used after 24 hours fasting. Six hours after oral administration of the test compound or vehicle of test compound (control), blood was collected into a tube containing 0.1 vol. of 3.8% sodium citrate and prepared platelet rich plasma (PRP).

To the 250 µl of PRP, 5 µl of arachidonic acid (final 50 µM) was added as an aggregation inducer. Aggregation was measured by using an aggregometer (NKK HEMA-TRACER 1). The following result shows the relationship between the dose of the test compound and the percentage (%) of its inhibitory activity against the platelet aggregation responses.

2. Test result

| Test compound | Dose (mg/kg) | Inhibition (%) |
|---|---|---|
| Example 1 | 1.0 | 100 |

Platelet aggregation in vitro (2)

1. Test method

Platelet rich plasma (PRP) which contains $6-7 \times 10^8$ platelets/ml and $3 \times 10^8$ platelets/ml was prepared from guinea-pig and human blood, respectively. To the each 245 μl of PRP, 5 μl of drug solution* was added, and then stirred for 2 min at 37° C. To the solution, 5 μl of collagen (0.5 μg/ml) was added as an aggregation inducer. Aggregation was measured by using an aggregometer (NKK HEMA-TRACER 1). Activities of inhibitors (test compounds) were expressed as $IC_{50}$ values i.e. doses required to inhibit the platelet aggregation responses by 50%.

Drug solution* — Test compounds were dissolved in a mixture of ethanol, polyethylene glycol and saline (1:1:2, V/V/V) and dimethylsulfoxide for guinea-pig and human blood, respectively.

2. Test result

| Test Compound | $IC_{50}$ (M) | |
|---|---|---|
| | guinea-pig | human |
| Example 14 | $4.2 \times 10^{-8}$ | $5.6 \times 10^{-7}$ |

Assay for thrombin activity

1. Test method

Thrombin activity was measured using the synthetic peptide substrate (S-2238, Kabivitrum).

After 900 μl of 0.1 M Tris-HCl buffer (pH 8.0), 100 μl of drug solution and 10 μl of 3U/ml thrombin were incubated at 37° C. for 5 min, 2 ml of 100 μM S-2238 was added.

The rate of increase in absorbance at 405 nM due to hydrolysis of S-2238 was measured with a spectrophotometer.

Inhibition (%) of drug was calculated as follows:

Inhibition (%) = $(S-B)/A \times 100$

A:Abs/min in the absence of drug
B:Abs/min in the presence of drug

2. Test result

| Compound | Concentration (M) | Inhibition (%) |
|---|---|---|
| Example 5 | $1.0 \times 10^{-4}$ | 92.2 |

Relaxation effort on isolated rat aorta

1. Test method

Helical strip of rat thoracic aorta was suspended in the organ bath containing Tyrode solution gassed with 95% $O_2$—5% $CO_2$ at 37° C. under 0.5 g load. Contraction was induced by addition of KCl solution (final concentration was 30 mM). After the tonus reached plateau, drug solution (dissolved in dimethyl sulfoxide) was added cumulatively and finally $10^{-4}$ M of papaverine was added to get maximum relaxation. Activities of the test compound were expressed as $ED_{50}$ values i.e. doses required to relax the isolated rat aorta by 50%.

2. Test result

| Test compounds | $ED_{50}$ (M) |
|---|---|
| Example 1 | $6.2 \times 10^{-6}$ |
| Example 3 | $3.0 \times 10^{-6}$ |
| Example 14 | $4.8 \times 10^{-6}$ |
| Example 21 | $2.4 \times 10^{-6}$ |

Assay for thrombin induced aggregation in human washed platelets

1. Test method

Blood was drawn from healthy volunteers into a plastic tube containing 1/10 volume of 3.8% sodium citrate and centrifuged at 120 g for 10 min to obtain platelet rich plasma (PRP). An equal volume of 25 mM Tris-HCl buffer (pH 7.4) containing 130 mM NaCl and 1.5 mM EDTA (buffer A) was added to the PRP, mixed and centrifuged at 1500 g for 10 min. The platelet pellet was suspended in buffer A and centrifuged at 1500 g for 5 min. The platelets were resuspended in 25 mM Tris-HCl buffer (pH 7.4) containing 130 mM NaCl and 0.3 mM EDTA and recentrifuged at 1500 g for 5 min. The platelets were finally suspended in Tyrode solution containing 0.3% bovine serum albumin and the platelet count was adjusted to $3 \times 10^8$/ml. To 247.5 μl of platelet suspension, 2.5 μl of drug solution was added and incubated for 2 min at 37° C. prior to addition of thrombin solution (final conc. 0.3–0.5 U/ml). Platelet aggregation was turbidometrically measured using a HEMA-TRACER 1.

2. Test results

| Compound | Concentration (M) | Inhibition of the aggregation (%) |
|---|---|---|
| Example 12 | $1.0 \times 10^{-5}$ | 100 |

Assay for cyclooxygenase inhibition

1. Test method

The microsomal fraction from sheep seminals vesicles was purchased from Ran Biochem (Israel). The reaction mixture consisted of 0.1 M Tris-HCl, pH 7.6, 1 mM epinephrine, 2mM glutathione, 240 μg of the microsomal enzyme, in a total volume of 200 μl. The reaction was started by the addition of 10 μM ($^{14}$C) arachidonic acid (120 nM), and incubated at 37° C. for 5 min. The reaction was stopped by the addition of 50 μl of 1 N HCl. The synthesized prostaglandins were extracted with 1.5 ml of ethylacetate. The ethyl acetate layer was dried with nitrogen gas, and dissolved in 100 μl of methanol. The microliters of the methanol solution were applied to a thin-layer plate (Merck, Kiesegel 60F), and developed with ethylacetate:acetate (100:2). The $PGE_2$ fraction was scraped out, and the radioactivity was counted with 10 ml of toluene scrintilator.

The activity of the test compound was expressed as $IC_{50}$ value i.e. doses required to inhibit the activity of cyclooxygenase by 50%.

2. Test result

| Compound | $IC_{50}$ (M) |
|---|---|
| Example 1 | $4.3 \times 10^{-7}$ |

Anti-SRS-A activity

1. Test method

Peritoneal exudate cells were collected from glycogen-injected SD rats and adjusted to $1 \times 10^7$ cells/ml with Tyrode's solution. One milliliter of the cell suspension was incubated with indomethacin (10 μg/ml) and each varied concentration of the test compound for 10 minutes and, then, further incubated with $Ca^{++}$-ionophore (A123187, 1 μg/ml) for 10 minutes. The supernatant was collected by centrifugation and the SRS-A (slow-reacting substance of anaphylaxis)activity was determined in terms of contractility of the isolated guinea pig ileum in the presence of mepyramine, atropine and methysergide.

The results were expressed in terms of the 50% inhibitory concentration to SRS-A synthesis or release from peritoneal exudate cells.

2. Test result

| Test Compound | Inhibitory Concentration $IC_{50}$ (μg/ml) |
|---|---|
| Example 1 | 6.283 |

Antiinflammatory activity

1. Test method

Five male Sprague-Dawly rats weighing 160–180 g were used per group. Paw edema was induced by subplanar injection of 1% carrageenin (0.1 ml/rat) into the right hind paw. The test drug was suspended in 0.5% methylcellulose and administered orally 60 minutes before phlogogen. Paw volume was measured with plethysmometer (Ugo Bazil Co., Ltd.) by water displacement immersing the paw to the lateral malleolus. The difference of paw volume before and 3 hours after the phlogogen was designated as edema volume. The data were analyzed statistically by student's t-test.

2. Test result

| Compound | Inhibition (%) (Dose: 100 mg/kg) |
|---|---|
| Example 1 | 36.2 |

Effect on stomach of rats

No lesion was observed in the stomachs of the rats, which were treated and given the compound of Example 1 (100 mg/kg) in a same way of the before-mentioned "Antiinflammatory activity".

Acute toxicity

Test on acute toxicy of the compound of Example 1 in rats by peroral administration was conducted, and the dead at dose of 100 mg/kg could not be observed.

Half-life period

The half-life period of the compound of the Example 1 in rats by intravenous administration (0.32 mg/kg) was observed as 4.51 hours (β-phase).

For therapeutic administration, the object compounds (I) of the present invention and pharmaceutically acceptable salts thereof are used in a form of the conventional pharmaceutical preparation in admixture with a conventional pharmaceutically acceptable carrier such as an organic or inorganic solid or liquid excipient which is suitable for oral, parenteral or external administration. The pharmaceutical preparation may be compounded in a solid form such as granule, capsule, tablet, dragee or suppository, or in a liquid form such as solution, suspension or emulsion for injection, ingestion, eye drops, etc. If needed, there may be included in the above preparation auxiliary substance such as stabilizing agent, wetting or emulsifying agent, buffer or any other commonly used additives.

The effective ingredient may usually be administered with a unit dose of 0.001 mg/kg to 500 mg/kg, preferably 0.01 mg/kg to 10 mg/kg, 1 to 4 times a day. However, the above dosage may be increased or decreased according to age, weight and conditions of the patient or the administering method.

The following preparations and examples are given only for the purpose of illustrating the present invention in more detail.

Preparation 1

To a mixture of toluene (40.0 l) and triethylamine (204 g), which was saturated by hydrogen sulfide was added portionwise ethyl cyanoformate (20.0 kg) at 0° to 5° C. with stirring. After the reaction mixture was stirred for 30 minutes at 25° to 30° C., it was cooled at 0° to 5° C. for 30 minutes. The resulting crystals were collected by filtration, washed with toluene and dried under reduced pressure to give ethyl 2-amino-2-thioxoacetate (24.2 kg).

mp: 64°–65° C.

Preparation 2

A mixture of 1,2-bis(4-methoxyphenyl)-2-chloroethanone (5.00 g) and ethyl 2-amino-2-thioxoacetate (3.44 g) in ethanol (30 ml) was refluxed for 4 hours. After allowing to cool to ambient temperature, the reaction mixture was filtered and washed with ethanol, and the filtrate was evaporated in vacuo. The residue was subjected to column chromatography on silica gel (300 g) and eluted with a mixture of hexane and ethyl acetate (8:1, V/V). The fractions containing the object compound were combined and concentrated under reduced pressure, and to give a oily compound of 4,5-bis(4-methoxyphenyl)-2-ethoxycarbonylthiazole (6.10 g).

IR (Nujol): 2850, 1730, 1710, 1660, 1605, 1570, 1510 $cm^{-1}$.

NMR ($CDCl_3$, δ): 1.4 (3H, t, J=7 Hz), 3.80 (3H, s), 3.82 (3H, s), 4.50 (2H, q, J=7 Hz), 6.85 (4H, m), 7.28 (2H, d, J=9 Hz), 7.5 (2H, d, J=9 Hz).

Preparation 3

2-Ethoxycarbonyl-4-(4-fluorophenyl)-5-(4-methylthiophenyl)thiazole (4.11 g) was obtained by reacting 2-bromo-1-(4-fluorophenyl)-2-(4-methylthiophenyl)ethanone (5.77 g) with ethyl 2-amino-2-thioxoacetate (3.40 g) according to a similar manner to that of Preparation 2.

mp: 111°–114° C.

IR (Nujol): 1700, 1600, 1590, 1500 $cm^{-1}$.

NMR (DMSO-$d_6$, δ): 1.36 (3H, t, J=7 Hz), 2.50 (3H, s), 4.42 (2H, q, J=7 Hz), 7.10–7.60 (8H, m).

MASS (M/Z): 373 (M+).

Preparation 4

To a mixture of lithium aluminium hydride (2.22 g) and tetrahydrofuran (200 ml) was added a solution of 4,5-bis(4-methoxyphenyl)-2-ethoxycarbonylthiazole (19.66 g) in tetrahydrofuran (200 ml) with stirring and ice-cooling, and the mixture was stirred for 30 minutes at −2° to 3° C. To the reaction mixture was added an aqueous solution of sodium sulfate (10 ml) very carefully. After filtration, the filtrate was evaporated in vacuo. The resulting residue was subjected to column chromatography on silica gel (480 g) and eluted with a mixture of chloroform and methanol. The fractions containing the object compound were combined and evaporated in vacuo to give an oil of 4,5-bis(4-methoxyphenyl)-2-hydroxymethylthizole (5.22 g).

IR (Nujol): 1600, 1570 cm$^{-1}$.

NMR (DMSO-d$_6$, δ): 3.74 (3H, s), 3.78 (3H, s), 4.75 (2H, d, J=6 Hz), 6.10 (1H, t, J=10 Hz), 6.88 (2H, d, J=8 Hz), 6.95 (2H, d, J=8 Hz), 7.24 (2H, d, J=8 Hz), 7.38 (2H, d, J=8 Hz).

MASS (M/Z): 327 (M+).

Preparation 5

A mixture of 4,5-bis(4-methoxyphenyl)-2-hydroxymethylthiazole (5.04 g) and manganese dioxide (35.0 g) in ethyl acetate (250 ml) was stirred at ambient temperature for 5.5 hours. After filtration, the filtrate was evaporated in vacuo, and the resulting residue was washed with hexane to give 4,5-bis(4-methoxyphenyl)-2-formylthiazol (3.25 g).

mp: 96°14 97° C.

IR (Nujol): 1690, 1680, 1610, 1570, 1510 cm$^{-1}$.

NMR (DMSO-d$_6$, δ): 3.77 (3H, s), 3.80 (3H, s), 6.95 (2H, d, J=8 Hz), 6.99 (2H, d, J=8 Hz), 7.35 (2H, d, J=8 Hz), 7.42 (2H, d, J=8 Hz), 9.95 (1H, s).

MASS (M/Z): 325 (M+).

Preparation 6

A suspension of 2-amino-4,5-bis(4-methoxyphenyl)-thiazole thiazole hydrochloride (35.7 g) in a mixture of N,N-dimethylformamide (60 ml) and toluene (60 ml) was added dropwise to a suspension of sodium hydride (60% dispersion in mineral oil) (4.58 g) in a mixture of N,N-dimethylformamide (60 ml) and toluene (60 ml) for 30 minutes at 0° C. with stirring. The reaction mixture was stirred at the same temperature for 30 minutes. A solution of benzoyl isothiocyanate (9.57 g) in a mixture of N,N-dimethylformamide (30 ml) and toluene (30 ml) was added dropwise to the above-mentioned reaction mixture at 0°~5° C., stirred for 1 hour and continued to stir at 5°~10° C. for 2 hours. Water (200 ml) was added thereto and the resulting mixture was extracted with ethyl acetate (200 ml). The extract was washed with water and brine. The resulting organic layer was dried and evaporated. The residue was crystallized from ethyl acetate to give 2-(3-benzoylthioureido)-4,5-bis(4-methoxyphenyl)thiazole (41.9 g).

mp: 184°-185° C. (dec.)

IR (Nujol): 3220, 1660, 1605 cm$^{-1}$

NMR (DMSO-d$_6$, δ): 3.75 (3H, s), 3.80 (3H, s), 6.8-8.2 (13H, m), 11.97 (1H, s).

Preparation 7

A solution of sodium hydroxide (0.36 g) in methanol (4.1 ml) was added to a solution of 2-(3-benzoylthioureido)-4,5-bis(4-methoxyphenyl)thiazole (4.3 g) and water (0.5 ml) in methanol (25 ml). The resulting mixture was stirred for 3 hours at 55°~60° C. The methanol was evaporated in vacuo and the residue was triturated with water. The precipitates were collected by filtration and dried to give 4,5-bis(4-methoxyphenyl)-2-thioureidothiazole (3.20 g).

mp: 229°-2310° C. (dec.).

IR (Nujol): 1600, 1560, 1510, 1500 cm$^{-1}$.

NMR (DMSO-d$_6$, δ): 3.69 (3H, s), 3.73 (3H, s), 6.7-7.5 (8H, m), 8.5 (2H, br s), 11.70 (1H, s).

MASS (M/A): m/z 371 (M+).

Preparation 8

A suspension of 2-amino-4,5-bis(4-methoxyphenyl)-thiazole hydrochloride (1.00 g) in N,N-dimethylformamide (5 ml) was added dropwise to a suspension of sodium hydride (60% dispersion in mineral oil) (0.13 g) in N,N-dimethylformamide (5 ml) at 0° C. for 30 minutes. The reaction mixture was stirred at room temperature for 30 minutes. After methyl isothiocyanate (2.19 ml) was added dropwise to the reaction mixture, the reaction mixture was stirred at 80° C. for 5.5 hours. After allowing to cool to room temperature, the resulting precipitates were collected by filtration, washed with diisopropyl ether and diethyl ether to give 4,5-bis(4-methoxyphenyl)2-(3-methylthioureido)thiazole (0.81 g).

mp: 201°-202° C.

IR (Nujol): 3380, 3170, 1610, 1590, 1570, 1510, 1490 cm$^{-1}$.

NMR (CF$_3$COOH, δ): 3.20 (3H, s), 4.00 (6H, s), 6.85-7.60 (8H, m).

EXAMPLE 1

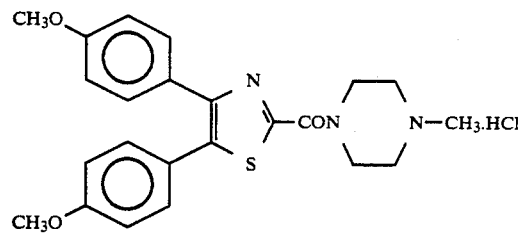

A mixture 4,5-bis(4-methoxyphenyl)-2-ethoxycarbonylthioazol (1.00 g) and N-methylpiperazine (1.80 ml was heated at 80°-90° C. for 62 hours. After allowing to cool to ambient temperature, the mixture was dissolved in dissolved in ethyl acetate and water. The separated organic layer was washed with water and brine, dried over magnesium sulfate and treated with activated charcoal.

After filtration, the filtrate was evaporated in vacuo, and the resulting residue was dissolved in diethyl ether and added ethanol solution of hydrogen chloride. The resulting precipitate was collected by filtration, washed with ethanol and diethyl ether and dried to give 4,5-bis(4-methoxyphenyl)-2-(4methylpiperazin-1-yl)carbonylthiazole hydrochloride (0.58 g).

mp: 248°-251° C.

IR (Nujol): 3400 (br), 2430, 1625, 1615, 1575, 1540, 1520 cm$^{-1}$.

NMR (DMSO-d$_6$, δ): 2.78 (3H, s), 3.00-3.70 (8H, m), 3.76 (3H, s), 3.79 (3H, s), 6.93 (2H, d, J=9 Hz), 6.99 (2H, d, J=9 Hz), 7.32 (2H, d, J=9 Hz), 7.42 (2H, d, J=9 Hz).

MASS (M/Z): 423 (M+ of free compound).

EXAMPLE 2

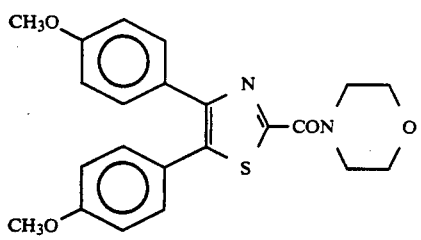

A mixture of 4,5-bis(4-methoxyphenyl)-2-ethoxycarbonylthiazole (1.00 g) and morpholine (1.42 ml) was heated at 80°–90° C. for 62 hours. After allowing to cool to ambient temperature, the mixture was dissolved in ethyl acetate and water. The separated organic layer was washed with water and brine, and dried over magnesium sulfate and treated with activated charcoal.

After filtration, the filtrate was evaporated in vacuo, and the resulting residue was triturated with ethanol and diethyl ether. The resulting crystals were washed with ethanol and diethyl ether, and dried to give 4,5-bis(4-methoxyphenyl)-2-morpholinocarbonylthiazole (0.28 g.

mp: 118°–122° C.

IR (Nujol): 1614, 1580, 1530, 1515 cm$^{-1}$.

NMR (DMSO-d$_6$, δ): 3.60–4.50 (14H, m), 6.95 (2H, d, J=9 Hz), 7.00 (2H, d, J=9 Hz), 7.30 (2H, d, J=9 Hz), 7.38 (2H, d, J=9 Hz).

MASS (M/A): 410 (M+).

EXAMPLE 3

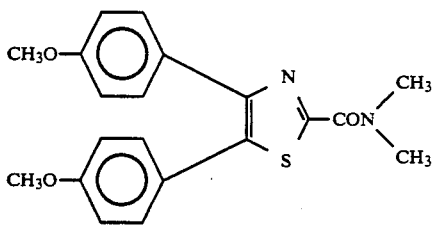

A mixture of 4,5-bis(4-methoxyphenyl)-2-ethoxycarbonylthiazole (1.50 g), dimethylamine hydrochloride (6.62 g) and triethylamine (11.32 ml) in ethanol (15 ml) was heated at 100° C. for 85 hours in a sealed tube. After allowing to cool to ambient temperature, the mixture was dissolved in ethyl acetate and water. The separated organic layer was washed with water and brine, dried over magnesium sulfate and treated with activated charcoal. After filtration, the filtrate was evaporated in vacuo. The residue was subjected to column chromatography on silica gel (75 g) and eluted with chloroform. The fractions containing the object compound were combined and evaporated in vacuo, to give a oily compound of 4,5-bis(4-methoxyphenyl)-2-(N,N-dimethylcarbamoyl)thiazole (0.36 g).

IR (Nujol): 1620, 1600, 1570, 1510 cm$^{-1}$.

NMR (DMSO-d$_6$, δ): 3.76 (3H, s), 3.79 (3H, s), 3.82 (6H, s), 6.84 (2H, d, J=6 Hz), 6.92 (2H, d, J=6 Hz), 7.15–7.48 (4H, m).

MASS (M/Z): 368 (M+).

EXAMPLE 4

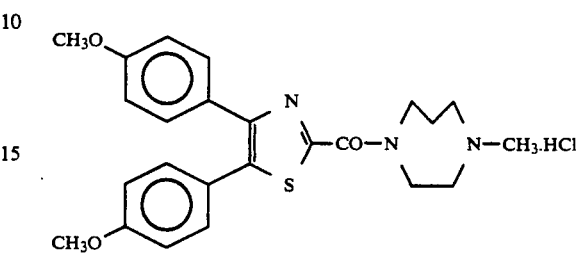

4,5-Bis(4-methoxyphenyl)-2-(4-methyl-1,4-perhydrodiazepin-1-yl)carbonylthiazole hydrochloride (0.54 g) was obtained by reacting 4,5-bis(4-methoxyphenyl)-2-ethoxycarbonylthiazole (0.57 g) with 1-methyl-1,4-perhydrodiazepine (1.15 ml) according to a similar manner to that of Example 1.

mp: 106°–116° C.

IR (Nujol): 1600, 1560, 1505 cm$^{-1}$.

NMR (DMSO-d$_6$, δ): 2.79 (3H, s), 3.05–4.60 (16H, m), 6.92 (2H, d, J=9 Hz), 6.99 (2H, d, J=9 Hz), 7.32 (2H, d, J=9 Hz), 7.41 (2H, d, J=9 Hz).

MASS (M/Z): 437 (M+ of free compound).

EXAMPLE 5

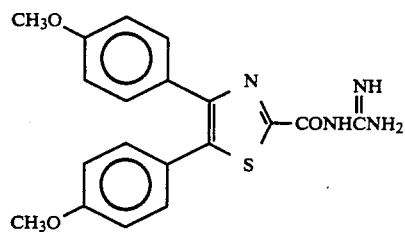

A mixture of guanidine (0.88 g) (which was taken from guanidine hydrochloride and sodium methoxide) and 4,5-bis(4-methoxyphenyl)-2-ethoxycarbonylthiazole (1.00 g) in methanol (10 ml) was stirred at ambient temperature for 2 hours.

The resulting crude precipitate was collected by filtration, washed with methanol, water, ethanol, and diethyl ether to give 4,5-bis(4-methoxyphenyl)-2-guanidinocarbonylthiazole (0.58 g).

mp: 253°–255° C.,

IR (Nujol): 3430, 3360, 3330, 3180, 1660, 1630, 1610, 1535, 1518 cm$^{-1}$.

NMR (DMSO-d$_6$, δ): 3.76 (3H, s), 3.78 (3H, s), 6.89 (2H, d, J=9 Hz), 6.95 (2H, d, J=9 Hz), 7.27 (2H, d, J=9 Hz), 7.36 (2H, d, J=9 Hz).

MASS (M/Z): 382 (M+).

EXAMPLE 6

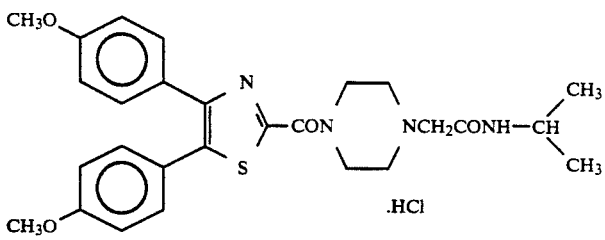

4,5-Bis(4-methoxyphenyl)-2-{4-(N-isopropylcarbamoylmethyl)piperazin-1-yl}carbonylthiazole hydrochloride (0.30 g) was obtained by reacting 4,5-bis(4-methoxyphenyl)-2-ethoxycarbonylthiazole (1.00 g) with 1-(N-isopropylcarbamoylmethyl)piperazine (3.01 g) according to a similar manner to that of Example 3.

mp: 124°–134° C.

IR (Nujol): 1665, 1603, 1550, 1505 cm$^{-1}$.

NMR (DMSO-d$_6$, δ): 1.15 (6H, d, J=6Hz), 3.2–4.4 (11H, m), 6.70–7.08 (4H, m), 7.11–7.50 (4H, m), 8.70 (1H, d, J=8 Hz).

MASS (M/Z): 508 (M+).

EXAMPLE 7

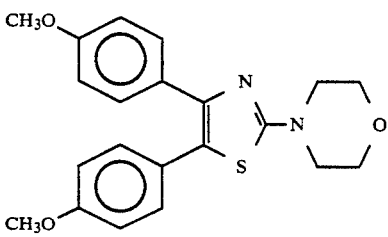

A mixture of 4,5-bis(4-methoxyphenyl)-2-chlorothiazole (0.5 g) and morpholine (1.31 ml) was heated at 80°–90° C. for 62 hours. After allowing to cool to ambient temperature, the mixture was dissolved in ethyl acetate and water. The separated organic layer was washed with water and brine, and dried over magnesium sulfate and treated with activated charcoal.

After filtration, the filtrate was evaporated in vacuo, and the resulting residue was washed with isopropyl ether, and dried to give 4,5-bis(4-methoxyphenyl)-2-morpholinothiazole (0.2 g).

mp: 133°–135° C.

IR (Nujol): 1610, 1570, 1530, 1510, 1490 cm$^{-1}$. NMR (DMSO-d$_6$, δ): 3.30–3.90 (14H, m), 6.83 (2H, d, J=9 Hz), 6.90 (2H, d, J=9 Hz), 7.18 (2H, d, J=9 Hz), 7.34 (2H, d, J=9 Hz).

MASS (M/Z): 382 (M+).

EXAMPLE 8

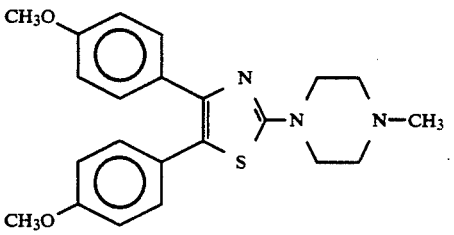

4,5-Bis(4-methoxyphenyl)-2-(4-methylpiperazin-1-yl)thiazole (0.30 g) was obtained by reacting 4,5-bis(4-methoxyphenyl)-2-chlorothiazole (0.5 g) with 4-methylpiperazine (1.67 ml) according to a similar manner to that of Example 7.

mp: 135°–136° C.

IR (Nujol): 1605, 1570, 1540, 1505, 1490 cm$^{-1}$.

NMR (DMSOd$_6$, δ): 2.23 (3H, s), 2.43–2.51 (4H, m), 3.30–3.45 (4H, m), 3.73 (3H, m), 3.75 (3H, m), 6.82 (2H, d, J=8.8 Hz), 6.89 (2H, d, J=8.8 Hz), 7.17 (2H, d, J=8.8 Hz), 7.34 (2H, d, J=8.8 Hz).

MASS (M/Z): 395 (M+).

EXAMPLE 9

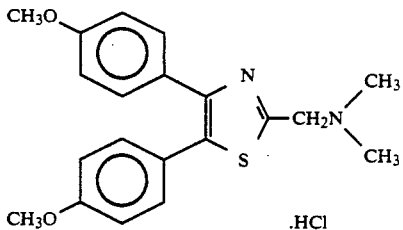

A mixture of 1,2-bis(4-methoxyphenyl)-2-chloroethanone (11.05 g) and 2-(N,N-dimethylamino)ethanethioamide 5.39 g) in ethanol (100 ml) was refluxed for 2 hours. After allowing to cool to room temperature, the solvent was evaporated in vacuo, and the residue was dissolved in chloroform (500 ml) and aqueous solution of sodium hydrogencarbonte (500 ml). The separated organic layer was washed with water and brine, dried over magnesium sulfate and treated with activated charcoal. After filtration, the filtrate was evaporated in vacuo. The resulting residue was dissolved in diethyl ether, added ethanol solution of hydrogen chloride, and the resulting precipitate was collected by filtration. The resulting crude compound was recrystallized with ethanol (30 ml). And the resulting crystal was collected by filtration, washed with ethanol and diethyl ether, and dried to give 4,5-bis(4-methoxyphenyl)-2-(N,N-dimethylaminomethyl)thiazole hydrochloride (2.85 g).

mp: 204°–207 ° C.

IR (Nujol): 2570, 2520, 2460, 1605, 1570, 1530, 1505, 1490 cm$^{-1}$.

NMR (DMSO-d$_6$, δ): 2.89 (3H, s), 3.76 (3H, s), 3.78 (3H, s), 4.70 (2H, s), 6.86 (2H, d, J=7 Hz), 6.95 (2H, d, J=7 Hz), 7.28 (2H, d, J=8 Hz), 7.40 (2H, d, J=8 Hz).

MASS (M/Z): 354 (M$^{30}$ of free compound).

EXAMPLE 10

[Structure: 2-aminomethyl-4,5-bis(4-methoxyphenyl)thiazole hydrochloride]

(1) 2-Acetylaminomethyl-4,5-bis(4-methoxyphenyl)-thiazole (2.52 g) was obtained by reacting 1,2-bis(4-methoxyphenyl)-2-chloroethanone (5.99 g) with 2-(acetylamino)ethanethioamide (3.00 g) according to a similar manner to that of Example 9.

mp: 138°–141° C.

IR (Nujol): 3270 (br s), 1750, 1650, 1610, 1520, 1510 cm$^{-1}$.

NMR (DMSO-d$_6$, δ): 1.95 (3H, s), 3.74 (3H, s), 3.81 (3H, s), 4.53 (2H, d, J=6 Hz), 6.90 (2H, d, J=7 Hz), 6.95 (2H, d, J=7 Hz), 7.25 (2H, d, J=8 Hz), 7.40 (2H, d, J=8 Hz), 8.80 (1H, t, J=6 Hz).

MASS (M/Z): 368 (M+).

(2) A mixture of 2-acetylaminomethyl-4,5-bis(4-methoxyphenyl)thiazole (1.80 g) and concentrated hydrochloride acid (10 ml) was refluxed for 50 minutes. After allowing to cool to ambient temperature, the mixture was poured into water. Then resulting solution was neutralized by addition of 4 N sodium hydroxide and extracted with ethyl acetate. The organic layer was washed with saturated sodium hydrogencarbonate solution, water and brine, and dried over magnesium sulfate and treated with activated charcoal. After filtration, the filtrate was evaporated in vacuo, and the resulting residue was dissolved in ethanol and added ethanol solution of hydrogen chloride.

The resulting mixture was added diethyl ether and triturated to give a powder.

This powder was washed with ethanol and diethyl ether to give 2-aminomethyl-4,5-bis(4-methoxyphenyl) hydrochloride (0.96 g).

mp: 141°–144° C.

IR (Nujol): 3350 (br), 1600, 1535, 1505 cm$^{-1}$.

NMR (DMSO-d$_6$, δ): 3.75 (3H, s), 3.79 (3H, s), 4.44 (2H, s), 6.90 (2H, d, J=9 Hz), 6.98 (2H, d, J=9 Hz), 7.27 (2H, d, J=9 Hz), 7.43 (2H, d, J=9 Hz).

MASS (M/Z): 326 (M+).

EXAMPLE 11

[Structure: 4,5-Bis(4-methoxyphenyl)-2-(4-pyridyl)thiazole]

4,5-Bis(4methoxyphenyl)-2-(4-pyridyl)thiazole (1.95 g) was obtained by reacting 1,2-bis(4-methoxyphenyl)-2-chloroethanone (3.00 g) with 4-(thiocarbamoyl)pyridine (1.57 g) according to similar manner to that of Example 9.

mp: 113°–117° C.

IR (Nujol): 1670, 1650, 1600, 1565, 1505 cm$^{-1}$.

NMR (DMSO-d$_6$, δ): 3.77 (3H, s), 3.79 (3H, s), 6.95 (2H, d, J=8 Hz), 6.99 (2H, d, J=8 Hz), 7.35 (2H, d, J=8 Hz), 6.48 (2H, d, J=8 Hz), 8.60–8.80 (4H, m).

EXAMPLE 12

[Structure: 4,5-bis(4-methoxyphenyl)-2-guanidinomethylthiazole hydrochloride]

A solution of 2-aminomethyl-4,5-bis(4-methoxyphenyl)thiazole hydrochloride (0.53 g) and cyanamide (0.61 g) in ethanol (15 ml) was refluxed for 16 hours with stirring. The reaction mixture was poured into water. The resulting solution was adjusted to pH 11 addition of an aqueous solution of potassium carbonate, and extracted with ethyl acetate. The extract was washed with brine and dried over magnesium sulfate and treated with activated charcoal.

After filtration, the filtrate was evaporated in vacuo. The resulting residue was dissolved with diethyl ether and added ethanol solution of hydrogen chloride. The resulting precipitate was collected by filtration and washed with diethyl ether, dried to give 4,5-bis(4-methoxyphenyl)-2-guanidinomethylthiazole hydrochloride (0.16 g).

mp: 103°–112° c.

IR (Nujol): 1640, 1635, 1603, 1505 cm$^{-1}$.

NMR (DMSO-d$_6$, δ): 3.75 (3H, s), 3.78 (3H, s), 4.82 (2H, d, J=5Hz), 6.89 (2H, d, J=8 Hz), 6.96 (2H, d, J=8 Hz), 7.26 (2H, d, J=8 Hz, 7.38 (2H, d, J=8 Hz), 7.71 (3H, br s), 8.58 (1H, br s).

MASS (M/Z): 369 (M+ of free compound.

EXAMPLE 13

[Structure: 4,5-bis(4-methoxyphenyl)-2-(1-methyl-1,2,3,6-tetrahydropyridin-4-yl)thiazole]

A solution of 4,5-bis(4-methoxyphenyl)-2-(4-pyridyl)-thiazole (1.78 g) and methyl iodide (2.96 ml) in a mixture of chloroform and methanol (5:2) (28 ml) was allowed to stand at ambient temperature for 2 days. The reaction mixture was evaporated in vacuo and the residue containing 4-[4,5-bis(4-methoxyphenyl)thiazol-2-yl]-1-methylpyridinium iodide was dissolved in a mixture of methanol (20 ml). To the resulting solution was added portionwise sodium borohydride (0.54 g) with stirring at 5° to 10° C. The reaction mixture was stirred for one hour at the same temperature. Water was added to the reaction mixture and the precipitate was collected by filtration. The precipitate was dissolved in chloroform and washed with brine and dried over magnesium sulfate. The solvent was evaporated in vacuo, and the residue was recrystallized from a aqueous methanol to give 4,5-bis(4-methoxyphenyl)-2-(1-methyl-1,2,5,6-tetrahydro-4-pyridyl)thiazole (0.16 g).

mp: 131°-132° C.

IR (Nujol): 1603, 1505, 1485 cm$^{-1}$,

NMR (DMSO-d$_6$, δ): 2.31 (3H, s), 2.60 (3H, br s), 3.31 (3H, s), 3.76 (3H, s), 3.78 (3H, s), 6.53 (1H, broad triplet), 6.83 (2H, d, J=8 Hz), 6.91 (2H, d, J=8 Hz), 7.22 (2H, d, J=9 Hz), 7.35 (2H, d, J=9 Hz).

MASS (M/Z): 392 (M+).

EXAMPLE 14

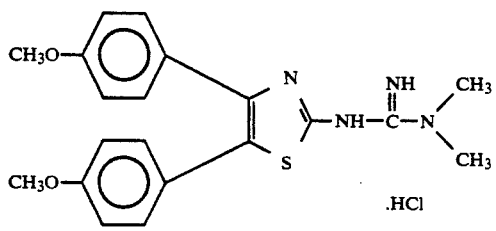

A mixture of 4,5-bis(4-methoxyphenyl)-2-thioureidothiazole (7.42 g) and methyl iodide (10 ml) in methanol (100 ml) was refluxed for 2 hours. The solvent was evaporated and the residue was dissolved in ethanol (50 ml). A mixture of above solution and dimethylamine hydrochloride (4.08 g) and triethylamine (5.06 g) were added in a sealed tube and the mixture was heated at 100° C. for 8 hours. The resulting mixture was evaporated in vacuo. The residue was dissolved in water and adjusted to pH 8 with sodium carbonate and extracted with a mixture of tetrahydrofuran and ethyl acetate. The extract was washed with brine (30 ml) and dried over magnesium sulfate. The solution was evaporated to dryness. The residue was chromatographed on silica gel eluting with 10% ethyl acetate in benzene. The desired fractions were combined, and the solvent was evaporated. The residue was crystallized from ethyl acetate solution containing hydrogen chloride to give 4,5-bis(4-methoxyphenyl)-2-(3,3-dimethylguanidino)-thiazole hydrochloride (1.27 g).

mp: 233°-235° C. (dec.)

IR (Nujol): 3250, 2650, 1665, 1630, 1605 cm$^{-1}$.

NMR (DMSO-d$_6$, δ): 3.27 (6H, s), 3.77 (6H, s), 6.8-7.6 (8H, m), 9.2 (2H, br s), 10.6 (4H, br s).

MASS (M/Z): 382 (M+ of free compound).

EXAMPLE 15

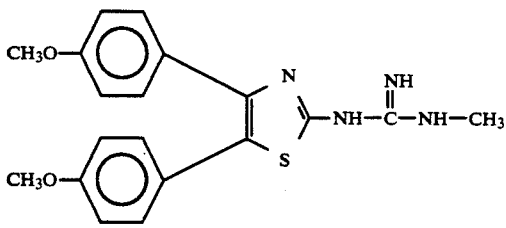

A mixture of 4,5-bis(4-methoxyphenyl)-2-thioureidothiazole (1.11 g) and methyl iodide (3 ml) in dry methanol (15 ml) was refluxed for 2 hours. The solvent was evaporated and the residue was dissolved with ethanol (15 ml). A mixture of above solution and, methylamine (4ml) was added in a sealed tube and heated at 80° C. for 4 hours. The resulting mixture was evaporated in vacuo. The residue was dissolved in a mixture of water (10 ml), ethyl acetate (20 ml) and tetrahydrofuran (10 ml). The organic layer was washed with brine and dried over magnesium sulfate, filtered and evaporated to dryness. The residue was chromatographed on silica gel eluting with 10% ethyl acetate in chloroform. The desired fractions were combined and the solvent was evaporated. The residue was crystallized from a mixture of ethyl acetate and diethyl ether to give 4,5-bis(4-methoxyphenyl)-2-(3-methylguanidino)thiazole (0.15 g).

mp: 155°-157° C.

IR (Nujol): 3400, 2150, 1660, 1590, 1530, 1510 cm$^{-1}$.

NMR (DMSO-d$_6$, δ): 2.74 (3H, d, J=5 Hz), 3.72 (6H, s), 6.80 (2H, d, J=9 Hz), 6.82 (2H, d, J=9 Hz), 7.12 (2H, d, J=9 Hz), 7.22 (2H, d, J=9H), 7.47 (1H, br s).

MASS (M/Z): 368 (M+).

EXAMPLE ≠

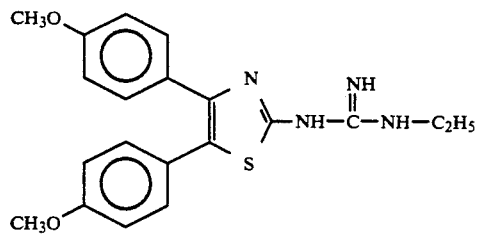

4,5-Bis(4methoxyphenyl)-2(3-ethylguanidino)-thiazole was obtained according to a similar manner to that of Example 15.

mp: 183°-185° C.

IR (Nujol): 3300, 1610, 1565, 1540, 1515, 1490 cm$^{-1}$.

NMR (DMSO-d$_6$, δ): 1.15 (3H, t, J=7 Hz), 3.20 (2H, q, J=7 Hz), 3.75 (6H, s), 6.75-7.60 (11H, m).

MASS (M/Z): 382 (M+).

EXAMPLE 17

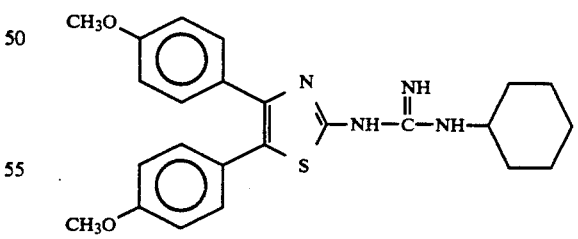

4,5-Bis(4-methoxyphenyl)-2-(3-cyclohexyl-guanidino)thiazole was obtained according to a similar manner to that of Example 15.

mp: 162°-164° C.

IR (Nujol): 3450, 3320, 1650, 1600, 1520, 1500 cm$^{-1}$.

NMR (DMSO-d$_6$, δ): 0.90-2.05 (11H, m), 3.80 (6H, s), 6.70-7.48 (11H, m).

MASS (M/Z): 436 (M+).

EXAMPLE 18

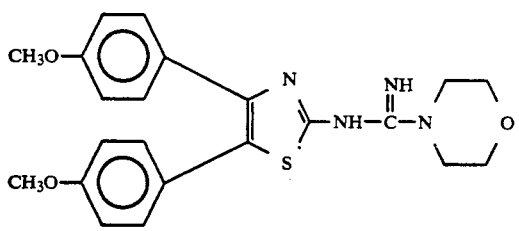

A mixture of 4,5-bis(4-methoxyphenyl)-2-thioureidothiazol (3.71 g) and methyl iodide (5 ml) in dry methanol (50 ml) was refluxed for 2 hours. The solvent was evaporated and the residue was dissolved in ethanol (30 ml). Morpholine (2.61 g) was added to the above solution and the resulting mixture was refluxed for 6 hours and allowed to stand overnight at ambient temperature. The mixture was filtered. The resulting solid was washed with ethanol (30 ml) to give 4,5-bis(4-methoxyphenyl)-2[N-(morpholine-4-carboximidoyl)amino]thiazole (2.16 g).

IR (Nujol): 3400, 1605, 1510, 1485 cm$^{-1}$.

NMR (DMSO-d$_6$, δ): 2.51 (4H, s), 3.0–3.2 (2H, m), 3.7–3.9 (2H, m), 3.70 (6H, s), 6.7–7.0 (4H, m), 7.1–7.4 (4H, m), 8.90 (1H, s).

MASS (M/Z): 424 (M+).

EXAMPLE 19

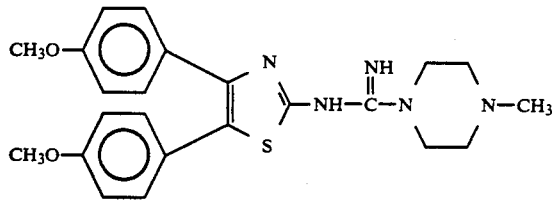

A mixture of 4,5-bis(4-methoxyphenyl)-2-thioureidothiazole (3.71 g) and methyl iodide (5 ml) in dry methanol (50 ml) was refluxed for 2 hours. The solvent was evaporated and the residue was dissolved in ethanol (30 ml). N-Methylpiperazine (5.0 g) was added to the above solution and the resulting mixture was heated at 100° C. for 8 hours. The reaction mixture was evaporated in vacuo. A mixture of water (20 ml) and ethyl acetate (20 ml) was added to the residue and the organic layer was washed with brine and dried over magnesium sulfate. The solvent was evaporated and the residue was chromatographed on silica gel eluting with 10% ethyl acetate in toluene. The desired fractions were combined and the solvent was evaporated. The residue was crystallized from methanol to give 4,5-bis(4-methoxyphenyl)-2-[N-{(imino)-(4-methylpiperazin-1-yl)methyl}amino]thiazole (0.96 g).

mp: 161°–162° C.

IR (Nujol): 3400, 1605, 1540, 1520 cm$^{-1}$.

NMR (DMSO-d$_6$, δ): 2.30 (3H, s), 2.3–2.7 (4H, m), 3.4–3.8 (4H, m), 3.60 (6H, s), 6.7–7.5 (8H, m), 8.30 (1H, s).

MASS (M/Z): 437 (M+).

EXAMPLE 20

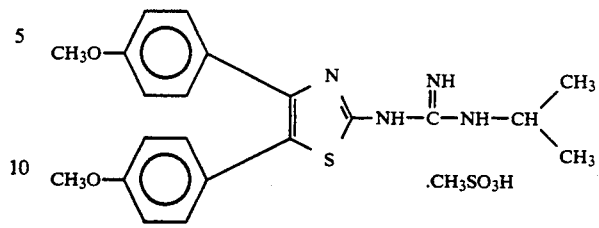

4,5-Bis(4-methoxyphenyl)-2-(3-isopropylguanidino)thiazole was obtained according to a similar manner to that of Example 15.

And the resulting compound was dissolved with diethyl ether and added methanesulfonic acid. The precipitate was collected by filtration, washed with a mixture of ethanol and diethyl ether, then dried to give 4,5-bis(4-methoxyphenyl)-2-(3-isopropylguanidino)thiazole methanesulfonate.

mp: 195°–197° C.

IR (Nujol): 1665, 1620, 1565, 1530, 1500, 1495 cm$^{-1}$.

NMR (DMSO-d$_6$, δ): 1.25 (6H, d, J=6 Hz), 2.48 (3H, s), 3.50–3.90 (7H, m), 6.78–7.55 (4H, m) 8.51–9.35 (3H, m).

MASS (M/Z): 396 (M+ of free compound).

EXAMPLE 21

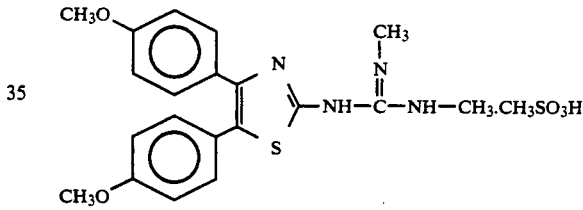

4,5-Bis(4-methoxyphenyl)-2-(2,3-dimethylguanidino)thiazole methanesulfonate was obtained according to a similar manner to that of Example 15 and 20.

mp: 231°–233° C.

IR (Nujol): 3140, 1675, 1630, 1610, 1575, 1545, 1510, 1490 cm$^{-1}$.

NMR (DMSO-d$_6$, δ): 2.25 (3H, s), 2.83 (3H, s), 2.90 (3H, s), 3.68 (6H, s), 6.71–7.42 (8H, m), 8.70 (2H, br s).

MASS (M/Z): 382 (M+).

EXAMPLE 22

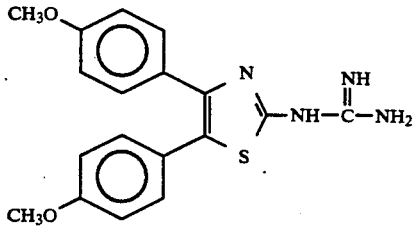

A mixture of 1,2-bis(4-methoxyphenyl)-2-chloroethanone (1.00 g) and N-diaminomethylenethiourea (0.65 g) in ethanol (20 ml) was refluxed for 12 hours. After allowing to cool to ambient temperature, then the reaction mixture was poured into water and extracted with ethyl acetate. The separated organic layer was washed with water and brine, dried over magnesium sulfate and evaporated in vacuo. The residue was chromatographed n alumina, eluting with a mixture of chloroform and methanol. The desired fractions were combined and concentrated in vacuo. The residue was washed with isopropy ether to give 4,5-bis(4methoxyphenyl)-2-guanidinothiazole (0.65 g).

mp: 121°–130° C.

IR (Nujol): 3450, 3100, 1655, 1610, 1535, 1515, 1495 cm$^{-1}$.

NMR (DMSO-d$_6$, δ): 3.70 (6H, s) 6.60–7.51 (12H, m).

MASS (M/Z): 354 (M+).

EXAMPLE 23

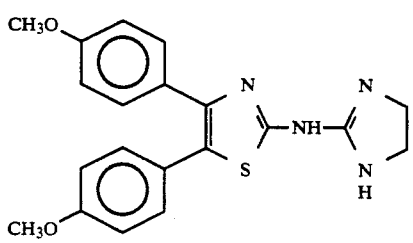

A mixture of 4,5-bis(4-methoxyphenyl)-2-thioureidothiazole (1.00 g) and methyl iodide (1.68 ml) in dry methanol (15 ml) and chloroform (15 ml) was refluxed for 2 hours. The solvent was evaporated and the residue was dissolved in ethanol (50 ml). A mixture of above solution and, ethylenediamine (1.80 ml) was added in a sealed tube and heated at 100° C. for 4 days. The resulting mixture was evaporated in vacuo. The residue was dissolved in a mixture of a saturated solution of sodium hydrogencarbonate and ethyl acetate. The organic layer was washed with brine and dried over magnesium sulfate, filtered and evaporated to dryness. The residue was crystallized from ethanol to give crystals of 4,5-bis(4-methoxyphenyl)-2-(2-imidazolin-2-yl)aminothiazole (0.46 g).

mp: 211°–214° C.

IR (Nujol): 3440, 3280, 3090, 1620, 1565, 1530, 1500 cm$^{-1}$.

NMR (DMSO-d$_6$, δ): 3.40–3.88 (10H, m), 6.72–7.75 (10H, m).

MASS (M/Z): 380 (M+).

EXAMPLE 24

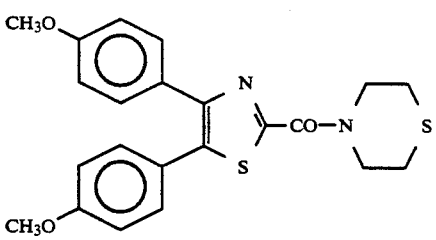

4,5-Bis (4-methoxyphenyl)-2-thiomorpholino carbonylthiazole was obtained according to a similar manner to that of Example 1.

mp: 150°–152° C.

IR (Nujol): 1650, 1610, 1510 cm$^{-1}$.

NMR (DMSO-d$_6$, δ): 2.76 (4H, br, s), 3.76 (3H, s), 3.78 (3H, s), 3.89 (2H, br s), 4.56 (2H, br s), 6.91 (2H, d, J=9 Hz), 6.98 (2H, d, J=9 Hz), 7.32 (2H, d, J=9 Hz), 7.38 (2H, d, J=9 Hz).

MASS (M/Z): 426 (M+).

EXAMPLE 25

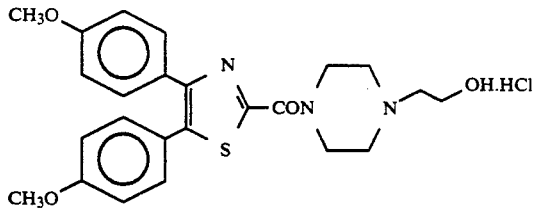

4,5-Bis(4-methoxyphenyl)-2{4-(2-hydroxyethyl)piperazin-1-ylcarbonyl}thiazole hydrochloride was obtained according to a similar manner to that of Example 1.

mp: 198°–201° C.

IR (Nujol): 1640, 1600, 1510 cm$^{-1}$.

NMR (DMSO-d$_6$, δ): 3.0–4.0 (9H, m), 3.76 (3H, s), 3.79 (3H, s), 4.55 (1H, m), 5.20–5.80 (2H, m), 6.92 (2H, d, J=8.9 Hz), 6.99 (2H, d, J=8.9 Hz), 7.32 (2H, d, J=8.9 Hz), 6.99 (2H, d, J=8.9 Hz), 11.14 (1H, s).

MASS (M/Z): 453 (M+ of free compound).

EXAMPLE 26

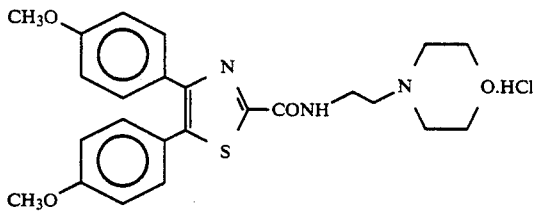

4,5-Bis(4-methyoxyphenyl)2(2-morpholinoethylcarbamoyl)thiazole hydrochloride was obtained according to a similar manner to that of Example 1.

mp: 249°–251° C. (decomp.).

IR (Nujol): 3250, 2470, 1660, 1610, 1530, 1520 cm$^{-1}$.

NMR (DMSO-d$_6$, δ): 3.00–4.10 (12H, m), 3.77 (3H, s), 3.79 (3H, s), 6.70 (2H, d, J=8.9 Hz), 6.92 (2H, d, J=8.9 Hz), 7.32 (2H, d, J=8.9 Hz), 7.48 (2H, d, J=8.9 Hz), 9.19 (2H, d, J=5.8 Hz),

MASS (M/Z): 453 (M+ of free compound).

EXAMPLE 27

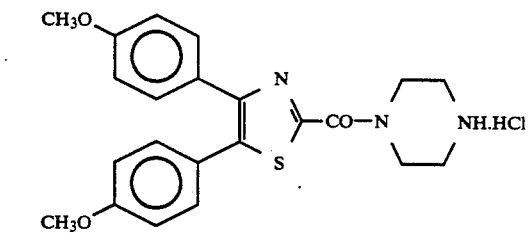

4,5-Bis(4-methoxyphenyl)-2-(piperazin-1-ylcarbonyl)thiazole hydrochloride was obtained according to a similar manner to that of Example 1.

mp: 109°–114° C.

IR (Nujol): 1620, 1605, 1510 cm$^{-1}$.

NMR (DMSO-d$_6$, δ): 3.3-3.6 (4H, m), 3.76 (3H, s), 3.79 (3H, s), 3.80-4.10 (2H, m), 4.50-4.80 (2H, m), 6.92 (2H, d, J=8.8 Hz), 6.98 (2H, d, J=8.8 Hz), 7.31 (2H, d, J=8.8 Hz). 7.40 (2H, d, J=8.8 Hz).

MASS (M/Z): 409 (M+ of free compound.

EXAMPLE 28

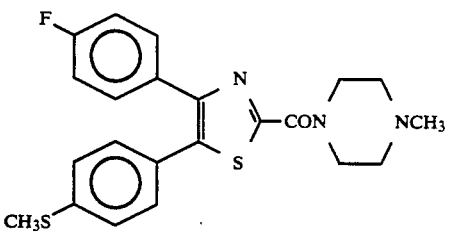

4-(4-Fluorophenyl)-2-(4-methylpiperazin-1-yl)carbonyl-4-(4-methylthiophenyl)thiazole was obtained according to a similar manner to that of Example 1.
mp: 140°-141° C.
IR (Nujol): 1625, 1610, 1600, 1500 cm$^{-1}$.
NMR (DMSO-d$_6$, δ): 2.21 (3H, s), 2.20-2.60 (4H, m), 2.50 (3H, s), 3.68 (2H, br s), 4.33 (2H, br s), 7.20-7.60 (8H, m).
MASS (M/Z): 425 (M+).

EXAMPLE 29

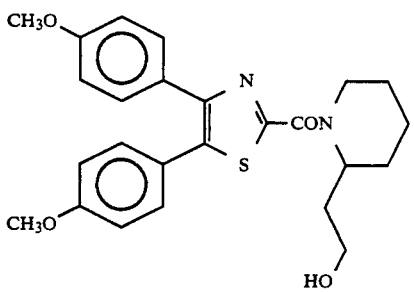

4,5-Bis(4-methoxyphenyl)-2-(R,S)-2-hydroxyethylpipidino)carbonylthiazole was obtained according to a similar manner to that of Example 2.
IR (Nujol): 3400, 1720, 1670, 1600, 1525, 1505 cm$^{-1}$.
NMR (DMSO-d$_6$, δ): 1.10-2.30 (8H, m), 3.35-3.60 (4H, m), 3.80 (3H, s), 3.83 (3H, s), 4.43 (1H, m), 6.90 (2H, d, J=9 Hz), 6.95 (2H, d, J=9 Hz), 7.31 (2H, d, J=9 Hz), 7.40 (2H, d, J=9 Hz), 8.30 (1H, s).
MASS (M/Z): 452 (M+).

EXAMPLE 30

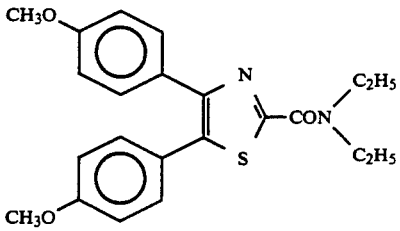

4,5-Bis(4-methoxyphenyl)-2-(N,N-diethylcarbamoyl)thiazole was obtained according to a similar manner to that of Example 2.
IR (Neat): 1600, 1570, 1500 cm$^{-1}$.

NMR (DMSO-d$_6$, δ): 1.17 (3H, t, J=6.9 Hz), 1.28 (3H, t, J=6.9 Hz), 3.48 (2H, q, J=6.9 Hz), 4.03 (2H, q, J=6.9 Hz), 3.76 (3H, s), 3.79 (3H, s), 6.91 (2H, d, J=8.9 Hz), 6.97 (2H, d, J=8.9 Hz), 7.32 (2H, d, J=8.9 Hz), 7.40 (2H, d, J=8.9 Hz).
MASS (M/Z): 396 (M+).

EXAMPLE 31

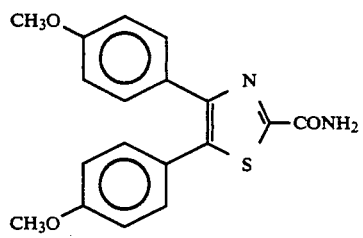

4,5-Bis(4-methoxyphenyl)-2-carbamoylthiazole was obtained according to a similar manner to that of Example 2.
mp: 160°-162° C.
IR (Nujol): 3400, 1680, 1610, 1510 cm$^{-1}$.
NMR (DMSO-d$_6$, δ): 3.76 (3H, s), 3.79 (3H, s), 6.90 (2H, d, J=8 Hz), 6.94 (2H, d, J=8 Hz), 7.30 (2H, d, J=8 Hz), 7.44 (2H, d, J=8 Hz), 7.87 (1H, s), 8.17 (1H, s),
MASS (M/Z): 340 (M+), 341 (M++1).

EXAMPLE 32

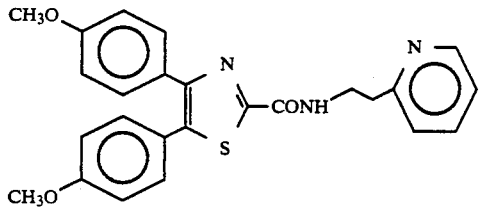

4,5-Bis(4-methoxyphenyl)-2-[2-(2-pyridyl)ethylcarbamoyl]thiazole was obtained according to a similar manner to that of Example 2.
mp: 130°-132° C.
IR (Nujol): 3210, 1660, 1605, 1590, 1570, 1530, 1510 cm$^{-1}$.
NMR (DMSO-d$_6$, δ): 3.05 (2H, t, J=7 Hz), 3.66 (2H, t, J=7 Hz), 3.77 (3H, s), 3.79 (3H, s), 6.92 (2H, d, J=8.9 Hz), 6.98 (2H, d, J=8.9 Hz), 7.20-7.60 (6H, m), 7.70 (1H, ddd, J=7.6 Hz, 5.8 Hz, 1.8 Hz), 8.52 (1H, d, J=4.8 Hz), 8.96 (1H, dd, J=7.6 Hz, 5.8 Hz).
MASS (M/A): 445 (M+).

EXAMPLE 33

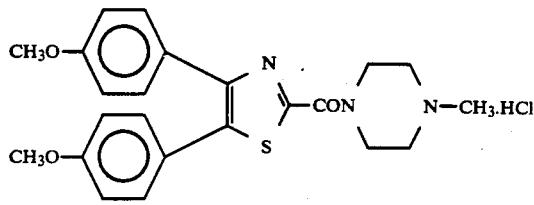

Crude crystals (23.82 g) of 4,5-bis(4-methoxyphenyl)-2-(4-methylpiperazin-1-yl)carbonylthiazole hydrocloride were obtained by heating 4,5-bis(4-methoxyphenyl)-2-ethoxycarbonylthiazole (22.1 g) and N-methylpiperazine (29.7 g) in ethylene glycol (21 g) under nitrogen gas at 75° C. for 4 hours and separating according to a similar manner to that of Example 1, and recrystallizing from isopropyl alcohol saturated with hydrogen chloride.

Further, these crude crystals (23 g) were recrystallized from a mixed solution of isopropyl alcohol and water (97:3, V/V) to give pure crystals (17.5 g) of 4,5-bis(4-methoxyphenyl)-2-(4-methylpiperazin-1-yl)carbonylthiazole hydrochloride.

mp: 248°–251° C.

EXAMPLE 34

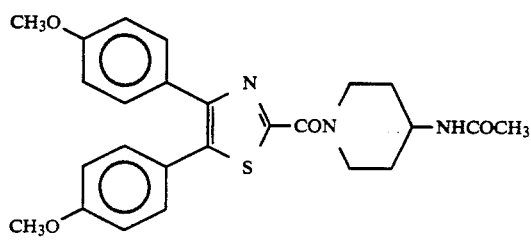

2-(4-Acetylaminopiperidin-1-yl)carbonyl-4,5-bis(4-methoxyphenyl)thiazole was obtained according to a similar manner to that of Example 1.

mp: 177°–180° C.

IR (Nujol): 3325, 1645, 1615, 1550, 1520 cm$^{-1}$.

NMR (DMSO-$d_6$, δ): 1.20–2.05 (4H, m), 1.81 (3H, s), 3.00–3.70 (2H, m), 3.76 (3H, s), 3.79 (3H, s), 3.80–4.00 (1H, m), 4.20–4.40 (1H, m), 5.00–5.20 (1H, m), 6.91 (2H, d, J=9 Hz), 6.98 (2H, d, J=9 Hz), 7.31 (2H, d, J=9 Hz), 7.38 (2H, d, J=9 Hz), 7.87 (1H, d, J=8 Hz),

EXAMPLE 35

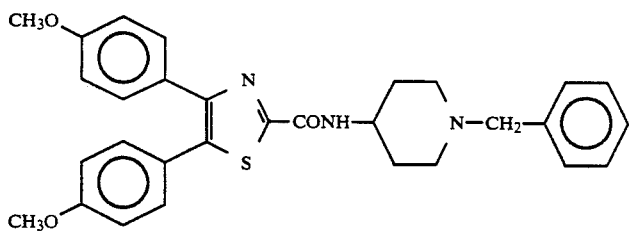

2-(1-Benzylpiperidin-4-yl)carbamoyl-4,5-bis(4-methoxyphenyl)thiazole was obtained according to a similar manner to that of Example 1.

mp: 130°–131° c.

IR (Nujol): 3400, 1670, 1615, 1580, 1525, 1490 cm$^{-1}$.

NMR (DMSO-$d_6$, δ): 1.60–1.90 (4H, m), 1.95–2.20 (2H, m), 2.70–3.00 (2H, m), 3.60 (2H, s) 3.76 (3H, s), 3.78 (3H, s), 6.91 (2H, d, J=9 Hz), 6.96 (2H, d, J=9 Hz), 7.20–7.40 (7H, m), 7.45 (2H, d, J=9 Hz), 8.62 (1H, d, J=8 Hz).

Mass (M/Z): 513 (M+).

EXAMPLE 36

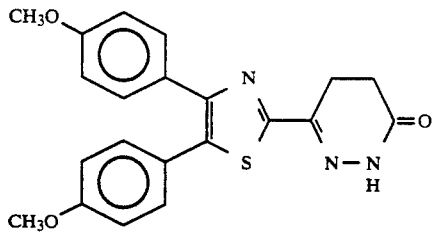

4,5-Bis(4methoxyphenyl)-2-(6-oxo-1,4,5,6-tetrahydropyridazin-3-yl)thiazole was obtained according to a similar manner to that of Example 9.

mp: 242°–247° C.

IR (Nujol): 3200, 3100, 1680, 1610, 1580, 1515 cm$^{-1}$.

NMR (DMSO$d_6$, δ): 2.50 (2H, t, J=8.4 Hz), 3.13 (2H, t, J=8.4 Hz), 3.76 (3H, s), 3.78 (3H, s), 6.90 (2H, d, J=8.9 Hz), 6.97 (2H, d, J=8.9 Hz), 7.29 (2H, d, J=8.9 Hz), 6.97 (2H, d, J=8.9 Hz)

MASS (M/Z): 353 (M+).

EXAMPLE 37

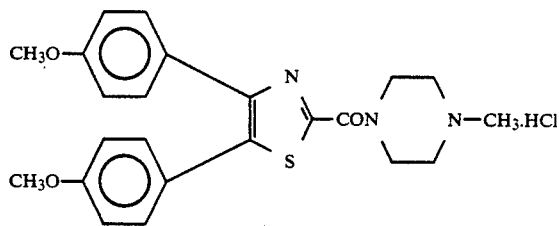

4,5-Bis(4-methoxyphenyl)-2-(4-methylpiperazin-1-yl) carbonylthiazole hydrochloride was obtained according to a similar manner to that of Example 9.

mp: 248°–251° C.

EXAMPLE 38

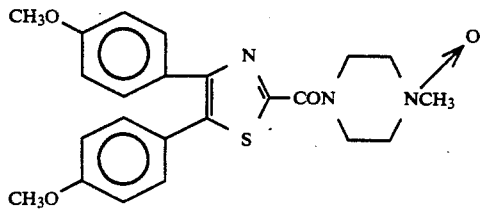

4,5-Bis(4-methoxyphenyl)-2-(4-methylpiperazin-1-yl)carbonylthiazole hydrochloride (2.00 g) was added to a mixture of dichloromethane and a saturated aqueous solution of sodium hydrogencarbonate, and 4,5- bis(4-methoxyphenyl)-2-(4-methylpiperazin-1-yl)carbonylthiazole was extracted with dichloromethane. The separated organic layer was washed with water and brine, and dried over magnesium sulfate. After filtration, the filtrate was evaporated in vacuo, and the resulting residue was dissolved with dichloromethane (20 ml). m-Chloroperoxybenzoic acid (0.90 g) was added thereto at ambient temperature, and the resulting mixture was stirred at ambient temperature for 2 hours. The reaction mixture was poured into an aqueous solution of sodium iodide, and the separated organic layer was washed with aqueous solution of sodium thiosulfate, saturated aqueous solution of sodium hydrogencarbonate, water and brine, and dried over magnesium sulfate. The resulting solution was treated with activated charcoal, and the filtrate was evaporated in vacuo. The residue was subjected to column chromatography on silica gel (100 g) an eluted with a mixture of chloroform and methanol. The fractions containing the object compounds were combined and evaporated in vacuo, and was washed with isopropyl ether to give 4,5-bis(4-methoxyphenyl)-2-(4-methyl-4-oxopiperazin-1-yl)arbonylthiazole (1.67 g).

mp: 199°–203° C.

IR (Nujol): 1615, 1605, 1505 cm$^{-1}$.

NMR (DMSO-d$_6$, δ): 2.85–3.90 (5H, m), 3.11 (3H, s), 3.76 (3H, s), 3.79 (3H, s), 4.05 (1H, m), 4.30 (1H, m), 5.35 (1H, m), 6.91 (2H, d, J=8.7 Hz), 6.98 (2H, d, J=8.7 Hz), 7.13 (2H, d, J=8.7 Hz), 7.39 (2H, d, J=8.7 Hz).

MASS (M/A): 439 (M+).

EXAMPLE 39

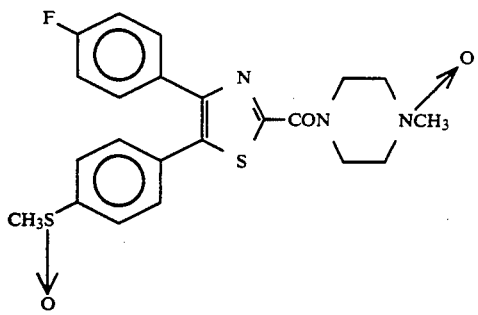

4-(4Fluorophenyl)-2-(4-methyl-4-oxopiperazin-1-yl)carbonyl-4-(4-methylsulfinylphenyl) thiazole (0.16 g) was obtaining by reacting 4-(4fluorophenyl)-2-(4-methylpiperazin-1yl)carbonyl-5-(4-methylthiophenyl) thiazole (0.70 g) with m-chloroperoxybenzoic acid (0.71 g) according to a similar manner to that of Example 38.

mp: 58°–62° C.

IR (Nujol): 1620, 1500 cm$^{-1}$.

NMR (DMSO-d$_6$, δ): 2.70 (3H, s), 3.10 (3H, s), 2.80–5.20 (8H, m), 6.90–7.90 (8H, m).

MASS (M/Z): 459 (M+).

EXAMPLE 40

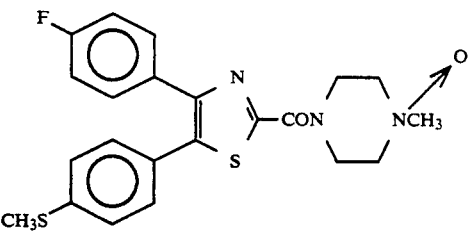

A mixture of 4-(4-fluorophenyl)-2-(4-methylpiperazin-1-yl)carbonyl-5-(4methylthiophenyl)-thiazole (1.00 g) and methanol (100 ml), water (1 ml) and sodium periodate (0.52 g) was stirred at ambient temperature for 31 hours. The reaction mixture was poured into water, and extracted with ethyl acetate. The separated organic layer was washed with an aqueous solution of sodium iodide, an aqueous solution of sodium thiosulfate, saturated aqueous solution of sodium hydrogencarbonate, water and brine in turn, and dried over magnesium sulfate. The resulting solution was treated with activated charcoal and the filtrate was evaporated in vacuo. The residue was subjected to column chromatography on silica gel (30 g) and eluted with a mixture of chloroform and methanol. The fractions containing the object compound were combined and evaporated in vacuo, and the resulting residue was triturated with isopropyl ether to give 4-(4-fluorophenyl)-2-(4-methyl-4oxopiperazin-1-yl)carbonyl-5-(4-methylthiophenyl) thiazole (0.03 g).

mp: 135°–139° C.

IR (Nujol): 1620, 1500 cm$^{-1}$.

NMR (DMSO-d$_6$, δ): 2.4 (3H, s), 3.0–4.1 (11H, m), 7.0–7.6 (8H, m).

MASS (M/Z): 441 (M+ −2).

EXAMPLE 41

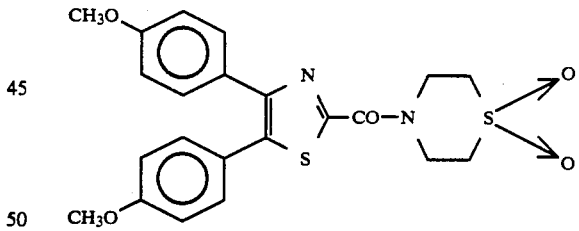

To a solution of 4,5-bis(4-methoxyphenyl)-2-thiomorpholinocarbonylthiazole (0.50 g) in dichloromethane (10 ml) was added m-chloroperoxybenzoic acid (0.68 g) and the resulting mixture was stirred for 5 hours at ambient temperature. To the reaction mixture was added a saturated aqueous solution of sodium hydrogencarbonate and the resulting mixture was extracted with dichloromethane. The separated organic layer was washed with a saturated aqueous solution of sodium iodide, a saturated aqueous solution of sodium thiosulfate, a saturated aqueous solution of sodium hydrogencarbonate, water and brine in turn, and dried over magnesium sulfate. The resulting solution was treated with activated in vacuo, and the resulting residue was washed with diethyl ether to give 4,5-bis(4-methoxyphenyl)-2-(1,1-dioxothiomorpholino)carbonylthiazole (0.38 g).

mp: 180°–182° C.
IR (Nujol): 1620, 1610, 1510 cm$^{-1}$.
NMR (DMSO-d$_6$, δ): 3.32 (4H, br s), 3.76 (3H, s), 3.78 (3H, s), 4.07 (2H, br s), 4.76 (2H, br s), 6.92 (2H, d, J=9 Hz), 6.99 (2H, d, J=9 Hz), 7.32 (2H, d, J=9 Hz), 7.39 (2H, d, J=9 Hz)
MASS (M/Z): 458 (M+).

EXAMPLE 42

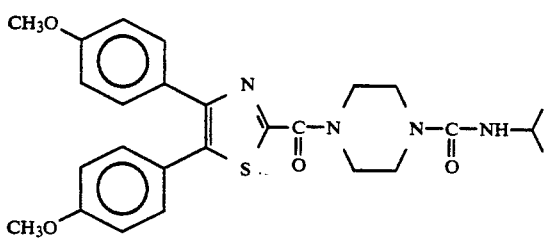

4,5-Bis(4-methoxyphenyl)-2-piperazin-1-ylcarbonyl-thioazole hydrochloride (1.00 g) was added to a mixture of dichloromethane and a saturated aqueous solution of sodium hydrogencarbonate, and 4,5-bis(4-methoxyphenyl)-2-piperazin-1-ylcarbonylthiazole was extracted with dichloromethane. The separated organic layer was washed with water and brine, and dried over magnesium sulfate. After filtration, the filtrate was evaporated in vacuo, and the resulting residue was dissolved with tetrahydrofuran (20 ml) and methanol (7 ml) N-Isopropyl isocyanate (0.38 ml) was added thereto, and the reaction mixture was stirred at ambient temperature for 90 minutes. The resulting mixture was evaporated in vacuo, and resulting powder was triturated with isopropyl ether to give 4,5-bis(4-methoxyphenyl)-2-(4-isopropylcarbamoylpiperazin-1-ylcarbonyl)thiazole (0.72 g).
mp: 157°–159° C.
IR (Nujol): 3280, 1610, 1530, 1510 cm$^-$.
NMR (DMSO-d$_6$, δ): 1.07 (6H, d, J=8 Hz), 3.44 (4H, br s), 3.65 (2H, br s), 3.76 (3H, s), 3.78 (3H, s), 4.37 (2H, br s), 6.28 (1H, d, J=8 Hz), 6.92 (2H, d, J=9 Hz), 6.98 (2H, d, J=9 Hz), 7.32 (2H, d, J=9 Hz), 7.39 (2H, d, J=9 Hz).
MASS (M/Z): 494 (M+).

EXAMPLE 43

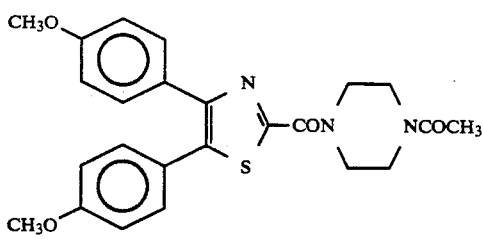

A mixture of 4,5-bis(4methyoxyphenyl)-2-piperazin-1-ylcarbonylthiazole hydrochloride (0.40 g) in dichloromethane (30 ml) was added to a saturated aqueous solution of sodium hydrogencarbonate, and extracted with dichloromethane. The separated organic layer was washed with brine and dried over magnesium sulfate. After filtration, the filtrate was evaporated in vacuo. The resulting residue was dissolved in a mixture of dichloromethane (10 ml) and triethylamine (0.14 ml). To the mixture was added dropwise a solution of acetyl chloride (0.07 ml) in dichloromethane (5 ml), at 0° to 5° C., and the reaction mixture was stirred at ambient temperature for 30 minutes. The resulting mixture was poured into water, and adjusted to pH 11 with aqueous solution of potassium carbonate, and extracted with dichloromethane. The separated organic layer was washed with a saturated aqueous solution of sodium hydrogencarbonate, water, dilute hydrochloric acid, water, and brine, and dried over magnesium sulfate and treated with activated charcoal. After filtration, the filtrate was evaporated in vacuo. The resulting residue was recrystallized from a mixture of isopropyl ether and ethanol to give a crystal of 2-(4acetylpiperazin-1-yl)carbonyl-4,5-bis(4methoxyphenyl)thiazole (0.18 g).
mp: 176°–178° C.
IR (Nujol): 1640, 1620, 1530 cm$^{-1}$.
NMR (DMSO-d$_6$, δ): 2.05 (3H, s), 3.59 (6H, br s), 3.76 (3H, s), 3.78 (3H, s), 4.35 (2H, br s), 6.92 (2H, d, J=9 Hz), 6.99 (2H, d, J=9 Hz), 7.32 (2H, d, J=9 Hz), 7.40 (2H, d, J=9 Hz).
MASS (M/A): 451 (M+).

EXAMPLE 44

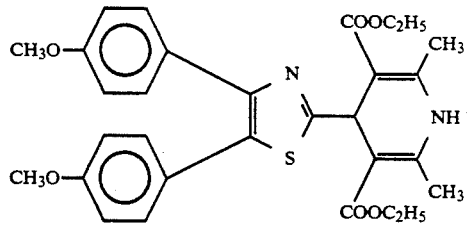

A mixture of 4,5-bis(4-methoxyphenyl)-2-formyl-thiazole (0.99 g), ethyl acetoacetate (0.43 ml) morpholine (0.027 ml), and acetic acid (0.017 ml) in benzene (10 ml) was stirred and refluxed for 30 minutes. After allowing to cool to room temperature, the mixture was poured into a mixture of ethyl acetate and water, and the separated organic layer was washed with water and brine, and dried over magnesium sulfate. After filtration, the filtrate was evaporated in vacuo. To the residue was added ethyl aminocrotonate (0.42 ml) and ethanol (10 ml), and the resulting mixture was stirred and refluxed for 13 hours. After allowing to cool to room temperature, the mixture was poured into a mixture of ethyl acetate and water, and the separated organic layer was washed with water, diluted hydrochloric acid, water and brine, and dried over magnesium sulfate. After filtration, the filtrate, was evaporated in vacuo. The resulting residue was subjected to column chromatography on alumina (13 g) and eluted with a mixture of benzene and ethyl acetate. The fractions containing the object compound were combined and concentrated under reduced pressure, and the resulting precipitate was washed with ethyl ether to give 4,5-bis(4-methoxyphenyl)-2-{3,5-bis(ethoxycarbonyl)-2,6-dimethyl-1,4-dihydropyridin -4-yl}-thiazole (0.17 g).
mp: 177°–178° C.
IR (Nujol): 1690, 1675, 1610, 1570, 1500 cm$^{-1}$.
NMR (DMSO-d$_6$, δ): 1.27 (6H, t, J=9 Hz), 2.34 (6 H, s), 3.75 (3H, s), 3.78 (3H, s), 4.25 (4H, q, J=9 Hz), 5.35 (1H, s), 6.80 (2H, d, J=9 Hz), 6.90 (2H, d, J=9 Hz), 7.18 (2H, d, J=9 Hz), 7.28 (2H, d, J=9 Hz), 9.03 (1H, s).
MASS (M/Z): 547 (M+).
What we claim is:
1. A compound of the formula

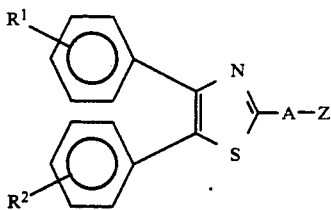

wherein

R¹ and R² are each halogen, lower alkyloxy, lower alkylthio, or lower alkylsulfinyl, A is lower alkylene, carbonyl, or single bond, and Z is a piperzinyl group which may have 1-4 substituents selected from the group consisting of lower alkyl, hydroxy(lower)alkyl, oxo, aliphatic acyl, aromatic acyl, acylamino, acyl(lower)alkyl, and esterified carboxy groups, or a pharmaceutically acceptable salt thereof.

2. The compound of claim 1, wherein Z is piperazinyl which may have 1-4 substituents selected from the group consisting of lower alkyl, hydroxy(lower)alkyl, oxo, lower alkanoyl, lower alkylcarbamoyl, lower alkanoylamino, lower alkylcarbamoyl(lower)alkyl, and lower alkoxycarbonyl.

3. A compound of claim 1, in which
R¹ and R² are each lower alkyloxy,
A is carbonyl, and
Z is piperazinyl which may have one or two substituents selected from lower alkyl, hydroxy(lower)alkyl, oxo, lower alkanoyl, lower alkylcarbamoyl and lower alkylcarbamoyl(lower)alkyl.

4. A compound of claim 3, in which
Z is 4-(lower)alkylpiperazinyl.

5. A compound of claim 4, which is 4,5-bis(4-methoxyphenyl)-2-(4-methylpiperazin-1-yl)carbonylthizole or its hydrochloride.

6. A compound of claim 1, wherein A is lower alkylene.

7. A compound of claim 1, wherein A is carbonyl.

8. A compound of claim 1, wherein A is a single bond.

9. A pharmaceutical composition comprising an effective amount of a compound of claim 1, in association with a pharmaceutically acceptable carrier or excipient.

10. A method for treatment of thrombosis, hypertension, allergy or inflammation which comprises administering an effective amount of the compound of claim 1 to an animal.

* * * * *